(12) United States Patent
Perez et al.

(10) Patent No.: US 8,026,413 B2
(45) Date of Patent: Sep. 27, 2011

(54) EMP4 GENE

(75) Inventors: Pascual Perez, Chanonat (FR); Gabriella Consonni, Olgiate Molgora (IT); Wyatt Paul, Aubiere (FR); Anna Giulini, Milan (IT); Christophe Tatout, Feurs (FR); Mauro Dal Prà, Verona (IT)

(73) Assignee: Biogemma, Paris (FR)

( * ) Notice: Subject to any disclaimer, the term of this patent is extended or adjusted under 35 U.S.C. 154(b) by 223 days.

(21) Appl. No.: 12/093,853

(22) PCT Filed: Nov. 14, 2006

(86) PCT No.: PCT/EP2006/068464
§ 371 (c)(1),
(2), (4) Date: Aug. 4, 2008

(87) PCT Pub. No.: WO2007/057402
PCT Pub. Date: May 24, 2007

(65) Prior Publication Data
US 2008/0313778 A1    Dec. 18, 2008

(30) Foreign Application Priority Data
Nov. 15, 2005   (EP) .................................... 05110763

(51) Int. Cl.
C12N 15/82    (2006.01)
A01H 5/00    (2006.01)
(52) U.S. Cl. .................... 800/298; 800/320.1; 800/278; 800/287; 800/290
(58) Field of Classification Search .................. None
See application file for complete search history.

(56) References Cited

U.S. PATENT DOCUMENTS
2006/0141495 A1*   6/2006   Wu .................................. 435/6

FOREIGN PATENT DOCUMENTS
WO   WO-03/008540 A2    1/2003
WO   WO 03/008540 A2 *  1/2003
WO   WO 03008540 A2 *   1/2003
WO   WO-2005/093077 A1  10/2005

OTHER PUBLICATIONS

Kano-Murakami et al (1993, FEBS 334:365-368).*
Bowie et al, Science 247:1306-1310, 1990.*
McConnell et al, Nature 411 (6838):709-713, 2001.*
Kim et al (2009, The Plant Journal 59:738-749).*

Dal Prá, M., et al., "A Mutation in the Pentatricopeptide Repeat-Containing Gene *Empty Pericarp-4* Affects Seed Development in Maize", Proceedings of the XLIX Italian Society of Agricultural Genetics Annual Congress, 2005.
Cushing, D. A., et al., "*Arabidopsis emb175* and Other *ppr* Knockout Mutants Reveal Essential Roles for Pentatricopeptide Repeat (PPR) proteins in Plant Embryogensis", Planta, 2005, vol. 221, pp. 424-436.
"Putative PPR Repeat Containing Protein", Database UniProtKB, Accession No. Q6ATJ2, Sep. 13, 2004.
"EMBL:AC135956", Database EBI, Accession AC135956, Oct. 27, 2002.
"EMBL:AP008209", Database EBI, Accession AP008209, Feb. 2, 2005.
Barkan, A., et al., "A Nuclear Mutation in Maize Blocks the Processing and Translation of Several Chloroplast mRNAs and Provides Evidence for the Differential Translation of Alternative mRNA Forms", The EMBO Journal, 1994, vol. 13, No. 13, pp. 3170-3181.
Fisk, D. G., et al., "Molecular Cloning of the Maize Gene *crp1* reveals Similarity Between Regulators of Mitochondrial and Chloroplast Gene Expression", The EMBO Journal, 1999, vol. 18, No. 9, pp. 2621-2630.
Fu, S., et al., "*Empty Pericarp2* Encodes a Negative Regulator of the Heat Shock Response and Is Required for Maize Embryogenesis", The Plant Cell, 2002, vol. 14, pp. 3119-3132.
Gutiérrez-Marcos, J. F., et al., "*Empty pericarp4* Encodes a Mitochondrion-targeted Pentatricopeptide Repeat Protein Necessary for Seed Development and Plant Growth in Maize", The Plant Cell Preview, 2007, pp. 1-15.
Consonni, G., et al., "Analysis of Four Maize Mutants Arrested in Early Embryogenesis Reveals an Irregular Pattern of Cell Division", Sex Plant Reprod, 2003, vol. 15, pp. 281-290.
Maitz, M., et al., "*rdf1*, A Mutation Reducing Grain Filling in Maize through Effects on Basal Endosperm and Pedicel Development", The Plany Journal, 2000, vol. 23, No. 1, pp. 29-42.
Scanlon, M., et al., "Genetic Analysis of 63 Mutations Affecting Maize Kernel Development Isolated from *Mutator* Stocks", Genetics, 1994, vol. 136, pp. 281-294.
Sheridan, W. F., et al., "Defective Kernel Mutants of Maize II. Morphological and Embryo Culture Studies", Genetics, 1980, vol. 95, pp. 945-960.
Scanlon, M. et al., "The maize gene empty pericap-2 is required for progression beyond early stages of embryogenesis", The Plant Journal, vol. 12, No. 4, pp. 901-909, 1997.
"Rice Abiotic Stress Responsive Polypeptide SEQ ID: 6093.", Database Geneseq, retrieved from EBI, Accession No. ABM87847, Jun. 2, 2005.
"EMBL:CL962709", Database EMBL, Accession CL962709, Sep. 22, 2004.
"Rice Abiotic Stress Responsive Polynucleotide SEQ ID No. 1962.", Database EBI, Accession No. ACL28006, Jun. 2, 2005.

* cited by examiner

*Primary Examiner* — Stuart F. Baum
(74) *Attorney, Agent, or Firm* — Connolly Bove Lodge & Hutz LLP

(57) ABSTRACT

The present invention relates to altering plant development and more particularly to altering the development of the plant endosperm. It concerns in particular nucleic acid molecules which alter the endosperm development.

7 Claims, 8 Drawing Sheets

D
| Maize EMP4 | 538 | LYNRQIAAEITEKVRKMAEERHVSFKMYKRRGVRDLEEKLKAKR...GQKKRSLR |
| Rice EMP4 | 553 | LYNRQIAAEITERVRKMAEERHVSFKMYKRRGVRDLEEKLKAKRRK.GQKRSRLR |
| At5g65820 | 583 | LYNRIIAGEITERVRNMAIERCISFKMYKRRGVDDLTEKAKSRODREGKKRQRSR |
| At3g49730 | 569 | LYNRTIAAEITEKVVKMASERLISFKMYKRRGEEDLIEKAKREGMKEGKKN... |
E
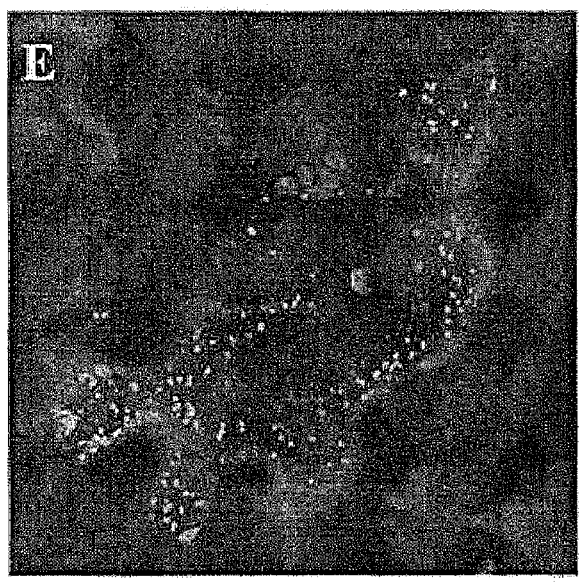
FIG. 5 contd

EMP4 GENE

RELATED APPLICATIONS

This application is a national stage application (under 35 U.S.C. 371) of PCT/EP2006/068464 filed Nov. 14, 2006, which claims benefit of European application 05110763.9 filed Nov. 15, 2005.

The present invention relates to altering plant development and more particularly to altering the development of the plant endosperm. It concerns in particular nucleic acid molecules which alter the endosperm development.

BACKGROUND OF THE INVENTION

The seed of cereals is one of the most economically important and scientifically interesting structure in plant biology. It consists of the embryo and the endosperm, the two products of the double fertilization event. The endosperm originates from the central cells of the embryo sac, which are fertilized by one of the two haploid male gametes, and the embryo originates from the fusion of the second gamete with the oosphere.

In maize, the embryo consists of an embryonic axis surrounded by a single massive cotyledon, the scutellum. The embryonic axis is characterized by the presence of a root primordium with the root meristem at the basis, the scutellar node, the mesocotyl and the shoot primordium comprising of the apical meristem and four-five leaf initials. The endosperm functions as an embryonic annex that sustains the embryo during its development and its germination.

The endosperm, a characteristic formation of Angiosperm seeds, is a nutritive tissue for the embryo. The maize endosperm originates with series of free-nuclear divisions, followed by cellularisation and the subsequent formation of a range of functional cellular domains. This tissue is complex in its structure and development, in particular in cereals.

The endosperm is the main storage organ in maize seeds, nourishing the embryo while the seed develops, and providing nutrients to the seedling on germination. Thus, the uptake of assimilates by the growing endosperm is a critical process in seed development.

The central area of the endosperm (first endosperm domain) consists of large cells with vacuoles, which store the reserves of starch and proteins (central starchy endosperm where genes involved in starch and in prolamin storage proteins biosynthesis are expressed), whilst the region surrounding the embryo (ESR that corresponds to the second endosperm domain) is distinguished by rather small cells, occupied for the major part by cytoplasm. The ESR may have a role in embryo nutrition or in establishing a physical barrier between the embryo and the endosperm during seed development.

The Basal Endosperm Transfer Layer (BETL that corresponds to the third endosperm domain) area is highly specialized to facilitate uptake of solutes during grain development. These transfer cells of the basal endosperm have specialised internal structures adapted to absorb solutes from the maternal pedicel tissue, and translocate these products to the developing endosperm and embryo. These transfer cells facilitate nutrient import into the maize kernel.

The fourth endosperm domain consists of the aleurone, which is the outer layer of the endosperm and accumulates proteins and oil.

The empty pericarp (emp) phenotype refers to a broad class of defective kernel (dek) mutants characterized by seeds exhibiting an extreme reduction in endosperm size, yet possessing a normal pericarp (Sheridan and Neuffer, 1980; Scanlon et al., 1994; Scanlon et al., 1997).

Scanlon et al. (1994) characterized a group of mutants presenting kernel with little or no endosperm. Such mutants, have aleurone present but no or little starchy endosperm.

To date, the molecular basis of only one emp phenotype ('empty pericarp') has been elucidated: the EMP2 gene, (Fu et al., 2002) which encodes a heat-shock response regulator. Absence of this protein in the null mutant leads to up regulation of hsp genes and is correlated with seed abortion.

The inventors here report a new gene allowing the alteration of the endosperm and plant development. This gene, EMP4 isolated from Mu tagged maize lines, encodes a PPR protein that is encoded in the nuclear genome but localised in the mitochondria. PPR proteins are often required for the maturation of organellar RNA and thus the EMP4 gene will regulate and will be limiting for efficient mitochondrial function and energy production at certain developmental stages or in certain cell types. Manipulation of EMP4 levels can thus alter the energy status and thus the growth of the cell, tissue, organ or plant either positively or negatively.

The present invention provides the first example of a maize PPR gene required for seed development. Moreover, the lesions in the EMP4 gene are associated with specific developmental defects, which are first recognizable in the highly metabolic cells of the endosperm basal transfer layer of emp4 mutants.

The mutation of the EMP4 gene confers a severe reduction in endosperm development and a seed lethal phenotype. Endosperm mutants are severely impaired, with differentiation of the nutrient importing basal endosperm transfer tissue being highly irregular. Homozygous mutants affected the general plant growth.

Such a nucleic acid molecule is particularly useful for enhancing yield via overexpression in cells, tissues or organs that are limiting for yield. In particular, the maize yield is thought to be limited by the sink strength of the developing kernels.

Advantageously, overexpression of the EMP4 gene in kernels or more specifically in the endosperm will increase sink strength via an increase in energy production in kernel cells and thus increase seed size.

The overexpression of the EMP4 gene is also useful for increasing plant growth rate, grain filling, starch and proteins accumulations, speeding seed development.

GENERAL DESCRIPTION

The present invention relates to an isolated nucleic acid molecule encoding a protein which alters the plant or endosperm development that comprises a sequence selected from the group consisting of:
a) a nucleotide sequence encoding a protein consisting of an amino acid sequence as depicted in SEQ ID No: 2 or an amino acid sequence that is at least 70% identical to SEQ ID No: 2, and variants thereof;
b) a nucleotide sequence as depicted in SEQ ID No: 1 or a nucleotide sequence that is at least 70% identical to SEQ ID No: 1;
c) a sequence hybridizing under stringent conditions with the complementary strand of a nucleic acid molecule as defined in (a) or (b).

The nucleic acid molecules according to the present invention will be called EMP4 nucleic acid molecules. The EMP4 nucleic acid molecules alter plant development or endosperm development.

The various nucleotide sequences of the invention can be of artificial origin or not. They may be DNA sequences obtained by screening libraries of sequences by means of probes produced on the basis of SEQ ID No: 1 or SEQ ID No: 3. Such libraries can be prepared by conventional techniques of molecular biology, known to persons skilled in the art.

The nucleotide sequences according to the invention can also be prepared by chemical synthesis, or by mixed methods including the chemical or enzymatic modification of sequences obtained by screening banks.

According to an embodiment of the invention, a nucleic acid molecule which alters the plant or endosperm development consists in SEQ ID No: 1.

According to an other embodiment of the invention, a nucleic acid molecule that alter the plant or endosperm development consists in a sequence going from nucleotide 10 (position 10) to nucleotide 1851 (position 1851) of SEQ ID No: 1.

According to another embodiment of the invention, a nucleic acid molecule which alters the plant or endosperm development consists in SEQ ID No: 4.

As used herein "variants" means that the sequence differs in one or more positions in comparison with the sequence SEQ ID No: 2 as long as it encodes a protein altering the plant or endosperm development, and possesses SEQ ID No: 28.

Such molecules comprise those which are variants of the EMP4 protein according to the invention and differ, for example, by way of amino acid and/or nucleotide deletion(s), insertion(s), substitution(s), addition(s) and/or recombination(s) or any other modification(s) known in the art either alone or in combination from the above described amino acid sequences or their underlying nucleotide sequence(s). Methods for introducing such modifications in the nucleic acid molecules according to the invention are well-known to the person skilled in the art. The invention also relates to nucleic acid molecules the sequence of which differs from the nucleotide sequence of any of the above-described nucleic acid molecules due to the degeneracy of the genetic code.

The invention further relates to a protein encoded by said nucleic acid molecules. More specifically, the invention provides a protein that alters the plant or endosperm development encoded by a nucleic acid molecule as defined above.

Preferably, a protein according to the invention may comprise, or consist in an amino acid sequence as depicted in SEQ ID No: 2.

Also preferably, such a protein consists in an amino acid sequence as depicted in SEQ ID No: 5.

The proteins encoded by the various variants of the above-described nucleic acid molecules share specific common characteristics, such as biological activity, molecular weight, conformation, etc., as well as physical properties, such as electrophoretic mobility, chromatographic behavior, sedimentation coefficients, pH optimum, temperature optimum, stability, solubility, spectroscopic properties, etc.

A nucleic acid molecule "hybridizes" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989).

Such an hybridizing sequence alters the plant or endosperm development according to the invention and contains at least 15, 25, 35, 37, 50, 75, 100, 121, 122, 127, 150, 200, 220, 240, 250, 270, 300, 350, 360, 365, 500, 750, 800, 900, 1000, 1100, 1200, 1300, 1400, 1500, 1600, 1700, 1800, 1850 nucleotides.

The invention also encompasses modifications of the DNA sequence as depicted in SEQ ID No: 1, or of sequence motifs thereof by, e. g., nucleotide replacements that do not affect the overall structure or the function of the nucleic acid molecule altering the plant or endosperm development so that it remains capable of altering the plant or endosperm development.

"Homologous nucleic acid sequence", or "homologous DNA sequence", means any nucleic acid sequence which differs from the sequence of reference by a substitution, deletion and/or insertion of one or more nucleotides at positions such that these homologous nucleic acid sequences preserve the possibility to alter plant or endosperm development.

Preferably, when the sequence of reference is SEQ ID No:1, such a homologous nucleic acid sequence is at least 70% identical to the sequence SEQ ID No: 1, preferably at least 85% identical, more preferably at least 90, 91, 95, 98, 99.9% identical. Also preferably, the degree of identity is defined by comparison with the entire sequence of reference, SEQ ID No: 1.

When the sequence of reference is SEQ ID No:2, such an identical protein is at least 70% identical to the sequence SEQ ID No: 2, preferably at least 79.8% identical, more preferably at least 85, 90, 91, 95, 98, 99.9% identical. Also preferably, the degree of identity is defined by comparison with the entire sequence of reference, SEQ ID No: 2. The present invention also relates to SEQ ID No: 5 that is 79.7% identical to SEQ ID No: 2. This percentage of identity has been obtained by the method of Needleman and Wunsch.

Homology is generally determined using a sequence analysis software (for example, the Sequence Analysis Software package of the Genetics Computer Group, University of Wisconsin Biotechnology Center, 1710 University Avenue, Madison, Wis. 53705). Similar nucleotide sequences are aligned in order to obtain the maximum degree of homology (i.e. identity). To this end, it may be necessary to artificially introduce gaps in the sequence. Once the optimum alignment has been achieved, the degree of homology (i.e. identity) is established by recording all the positions for which the nucleotides of the two compared sequences are identical, with respect to the total number of positions.

The preferred method uses the algorithm of Needleman and Wunsch.

In a preferential manner such a homologous nucleic acid sequence specifically hybridizes to a sequence which is complementary to the sequence SEQ ID No: 1 under stringent conditions. The parameters defining the stringency conditions depend on the temperature at which 50% of the paired strands separate (Tm).

For sequences comprising more than 30 bases, Tm is defined by the equation: $Tm=81.5+0.41(\% G+C)+16.6 \text{ Log (concentration in cations)}-0.63(\% \text{ formamide})-(600/\text{number of bases})$ (Sambrook et al., 1989).

For sequences shorter than 30 bases, Tm is defined by the equation: $Tm=4(G+C)+2(A+T)$.

Under appropriate stringency conditions, in which non-specific (aspecific) sequences do not hybridize, the temperature of hybridization is approximately between 5 and 30° C., preferably between 5 and 10° C. below Tm and hybridization buffers used are preferably solutions of higher ionic force like a solution 6*SSC for example.

Particularly, the EMP4 isolated nucleic acid molecule encodes a protein that alters the plant or endosperm development.

Preferably, the EMP4 nucleic acid molecule altering the plant or endosperm development consists in SEQ ID No: 1.

The EMP4 nucleic acid molecules according to the invention can be isolated from various plant species, notably Angiosperm plants, Monocotyledons or Dicotyledons and are preferably nucleic acid molecules isolated from a cereal or an oily plant. Still preferably, the nucleic acid molecules are isolated from a plant selected from the group consisting of maize, rice, sorghum, wheat, barley, rye, *brassica napus*, pea, sunflower and sugar cane. Still preferably, the plant is maize.

It is possible for the person skilled in the art to isolate with the help of the EMP4 nucleotide sequence of the invention, corresponding genes from other species.

This can be done by conventional techniques known in the art, for example, by using a sequence as depicted in SEQ ID No: 1 as a hybridization probe or by designing appropriate PCR primers.

It is possible to start with coding DNA sequences or Protein sequences via TBLASTN queries. The approach used to isolate rice EMP4 genes, for example, is to use the Protein sequence of EMP4, do a TBLASTN with this sequence against Rice ESTs, then use this EST to find the genomic sequence or directly use TBLASTN against the rice genome sequence. The same approach is used to isolate other EMP4 genes from other species.

Another object of the present invention is a nucleotide construction, referred to as an expression cassette comprising an EMP4 nucleic acid molecule as defined above operatively linked to regulatory elements allowing the expression in prokaryotic and/or eukaryotic host cells.

"Operatively linked" refers to functional linkage between an EMP4 nucleic acid molecule (altering the plant or endosperm development) according to the invention and a promoter sequence (regulatory element having a promoter activity).

The EMP4 nucleic acid molecule can be placed in the sense or antisense orientation.

The promoter sequence can be of a heterologous origin.

Any suitable promoter could be used. It could be a constitutive promoter. It could also be for example a tissue-specific promoter such as a seed-specific or a BETL-specific promoter. Numerous tissue-specific promoters are described in the literature and any one of them can be used.

Among constitutive promoters, one can use for example the CsVMV promoter (Verdaguer et al, 1996), the rice actin promoter (McElroy et al, 1990), the CAMV 35 S or the 19S promoter (Kay et al, 1987).

Preferably, the promoter used allows expression in the endosperm. More preferably, the promoter used allows expression in the BETL and still more preferably, the promoter is BETL-specific.

Advantageously, promoters are for example pMRP1 which is expressed in the central cell and in the BETL region prior to and after BETL cellularisation (Gomez et al (2002)), pMEG1 (Gutierrez-Marcos et al 2004), pBETL1 (Hueros et al 1999) and pBETL2 (WO 99/50427) which are BETL-specific promoters.

"BETL-specific promoter" means, as used in the present invention, that the promoter has a predominant pattern expression in the BETL, and preferably an exclusive pattern expression in the BETL.

The said EMP4 nucleic acid molecule can also be associated with other regulating elements such as transcription termination sequences (terminators). By way of examples of such sequences, it is possible to cite the polyA 35S terminator of the cauliflower mosaic virus (CaMV), described in the article of Franck et al. (1980) and the NOS terminator corresponding to the region in the non-coding 3' region of the nopaline synthase gene of the Ti-plasmid of the *Agrobacterium tumefaciens* nopaline strain (Depicker et al. 1992).

Preferably, the terminator used is the Nos terminator.

According to the invention, the expression cassette, comprising an EMP4 nucleic acid molecule as defined above, operatively linked to regulatory elements allowing the expression in prokaryotic and/or eukaryotic host cells (such as a promoter sequence) may further comprise one or several selection marker genes for plants, useful for transformation and selection.

In the present invention, the term "selectable marker", "selectable gene", "selectable marker gene", "selection marker gene", "marker gene" are used interchangeably.

These selectable markers include, but are not limited to, antibiotic resistance genes, herbicide resistance genes or visible marker genes. Other phenotypic markers are known in the art and may be used in this invention.

A number of selective agents and resistance genes are known in the art.

Notably the selectable marker used can be the bar gene conferring resistance to bialaphos (White et al., 1990), the sulfonamide herbicide Asulam resistance gene, sul (described in WO 98/49316) encoding a type I dihydropterate synthase (DHPS), the nptII gene conferring resistance to a group of antibiotics including kanamycin, G418, paromomycin and neomycin (Bevan et al., 1983), the hph gene conferring resistance to hygromycin (Gritz et al., 1983), the EPSPS gene conferring tolerance to glyphosate (U.S. Pat. No. 5,188, 642), the HPPD gene conferring resistance to isoxazoles (WO 96/38567), the gene encoding for the GUS enzyme, the green fluorescent protein (GFP), expression of which, confers a recognisible physical characteristic to transformed cells, the chloramphenicol transferase gene, expression of which, detoxifies chloramphenicol.

Advantageously, the selectable marker gene is inserted between a promoter and a terminator in a second expression cassette. Said second expression cassette being integrated in the same vector as the expression cassette containing the EMP4 nucleic acid molecule under transcriptional control of a promoter according to the invention.

According to this advantageous embodiment, the marker gene is preferably controlled by a promoter which allows expression in cells, thus allowing selection of cells or tissue containing the marker at any stage of development of the plant. Preferred promoters are the promoter of nopaline synthase gene of *Agrobacterium*, the promoter derived from the gene which encodes the 35S subunit of cauliflower mosaic virus (CaMV) coat protein, and the rice actin promoter. However, any other suitable second promoter may be used.

Any terminator may be used. Preferred terminators are the 3'CaMV and Nos terminator as previously described.

Advantageously, the expression cassette containing the selectable marker gene is comprised between two Ds elements (transposons) in order for its removal at a later stage by interacting with the Ac transposase. This elimination system is described in Yoder et al. (1993).

For the transformation step, two vectors could be used, the first one comprising the expression cassette containing the EMP4 nucleic acid molecule and the second one comprising the expression cassette containing the selectable marker gene. The same host cell being transformed with these two vectors (co-transformation).

The expression cassettes according to the invention may additionally contain transit peptide sequences. There are numerous examples in the art of transit peptides which may be used to deliver a target protein into a plastid organelle such as the small subunit (SSU) transit peptide of ribulose biphosphate carboxylase.

Other elements like introns and enhancers can also be present in the nucleic sequence of interest in order to improve the expression of the gene of interest.

Among useful introns, the first intron of maize adh1S can be placed between the promoter and the coding sequence. This intron when included in a gene construct increased the expression of the desired protein in maize cells. One also can use the 1$^{st}$ intron of the shrunken 1 gene of the maize (Maas et al., 1991), the 1$^{st}$ intron of the catalase gene of the bean catalase (CAT-1) (Ohta et al., 1990), the 2$^{nd}$ intron of the ST-LS1 gene of potato (Vancanneyt et al. 1990), the DSV intron of the yellow dwarf virus of tobacco (Morris et al., 1992), the actin-1 intron (act-1) of rice (McElroy et al., 1990), FAD 2 intron (WO 2006/003186) and intron 1 of triosephosphate isomerase (TPI) (Snowdon et al., 1996).

Preferentially, the intron used in the present invention is the Sh1 intron.

The expression cassettes may additionally contain 5' leader sequences. Such leader sequences can act to enhance translation, Such 5' leader sequences are known in the art and include, but are not limited to, picornavirus leaders, for example, the EMCV leader (Encephalomyocarditis 5' non-coding region) (Elroy-Stein, Fuerest, and Moss B., 1989); potyvirus leaders, for example, the TEV leader (Tobacco etch Virus) (Allison et al., 1986); the human immunoglobulin heavy-chain binding protein leader (BiP) (Macejack and Sarnow, 1991); the untranslated leader from the coat protein mRNA of alfalfa mosaic virus (AMV RNA 4) (Jobling and Gehrke, 1987); the tobacco mosaic virus leader (TMV) (Gallie et al., 1989); and the maize chlorotic mottle virus leader (MCMV) (Lommel et al., 1991). See also, Della-Cioppa et al. (1987). Other methods known to enhance translation can be utilized, for example introns, and the like.

In preparing the expression cassettes, the various DNA sequences or fragments may be manipulated, so as to provide DNA sequences or fragments in the proper orientation and, as appropriate, in the proper reading frame. Towards this end, adapters or linkers may be employed to join the DNA fragments and/or other manipulations may be required to provide convenient restriction sites, removal of superfluous DNA, removal of restriction sites, or the like. For this purpose, in vitro mutagenesis, primer repair, restriction, annealing, ligation, PCR, or the like may be employed, where nucleotide insertions, deletions or substitutions, for example transitions and transversions, may be involved. These techniques are well known by those skilled in the art.

Another object of the invention is any nucleotide vector referred to as an expression vector, such as a plasmid, which can be used for transforming host cells, characterized in that it contains at least an expression cassette as defined above. The construction of expression vectors for the transformation is within the capability of one skilled in the art following standard techniques.

The decision as to whether to use a vector, or which vector to use, is guided by the method of transformation selected, and by the host cell selected.

Where a naked nucleic acid introduction method is used, then the vector can be the minimal nucleic acid sequences necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis, K B (1987), *Methods in Enzymology*).

For other transformation methods requiring a vector, selection of an appropriate vector is relatively simple, as the constraints are minimal. The apparent minimal traits of the vector are that the desired nucleic acid sequence be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenic plants.

The vector can exist, for example, in the form of a phage, a plasmid or a cosmid. The construction of such expression vectors for transformation is well known in the art and uses standard techniques. Mention may be made of the methods described by Sambrook et al. (1989).

Another object of the invention is a host cell, containing at least an expression vector as described above.

The decision as to whether to use a host cell, or which host cell to use, is guided by the method of transformation.

The host cell can be any prokaryotic or eukaryotic cell. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*. A plant host cell, may be also used, notably an Angiosperm plant cell, Monocotyledon as Dicotyledon plant cell, particularly a cereal or oily plant cell, and more particularly selected from the group consisting of maize, wheat, barley, rice, rape, *Brassica napus*, sugar cane, sorghum, pea and sunflower. Still preferably the plant host cell is from maize.

More particularly, the host cell used in carrying out the invention is *Agrobacterium tumefaciens*, according to the method described in the article of An et al., 1986, or *Agrobacterium rhizogenes*, according to the method described in the article of Jouanin et al., 1987.

The invention also concerns a transgenic plant, or a part of a transgenic plant, comprising stably integrated into its genome a nucleic acid molecule according to the present invention operatively linked to regulatory elements allowing transcription and/or expression of the nucleic acid molecule in plant cells. "Part of a transgenic plant", according to the present invention, means in particular fruit, seed, grain, or pollen.

The invention also concerns a transgenic plant, or a part of a transgenic plant, comprising such a host cell or generated from such a host cell.

Where the plant contains endogenously an EMP4 gene according to the invention, it will be understood that the transgenic plant according to the invention comprises an additional "exogenous" EMP4 gene, for instance integrated by transgenese.

A whole plant can be regenerated from a single transformed plant cell. Thus, in a further aspect the present invention provides transgenic plants (or parts of them) including nucleic acid molecules in accordance with the invention. The regeneration can proceed by known methods.

The seeds which grow, by fertilization, from this plant also contain this transgene in their genome.

Advantageously, the transgenic plant obtained can produce grains with a larger (bigger) endosperm (increased endosperm size) in comparison with a non-transformed plant. In addition to increases in yield such transgenic plants may have grains with modified starch, oil or protein contents. In particular, said modification in starch, oil, or protein contents consists in an increase of starch, oil, or protein accumulation.

A plant or part of a plant according to the invention could be a plant or a part of it from various species, notably an Angiosperm, Monocotyledons as Dicotyledons, preferably a cereal or oily plant, and more preferably selected from the group consisting of maize, rice, sorghum, wheat, barley, rape, *brassica napus*, sugar cane, and sunflower. Still preferably, the plant is maize.

As used herein, the term "oily plant" denotes a plant that is capable of producing oil, and preferably that is cultivated for oil production.

The hybrid plants obtained by crossing plants according to the invention also form part of the invention.

The present invention also relates to a protein encoded by a nucleic acid molecule according to the invention.

Preferably, the protein consists of an amino acid sequence as depicted in SEQ ID No: 2, or being at least 70% identical to SEQ ID No: 2.

Also preferably, such a protein consists in SEQ ID No: 5.

An other object of the invention is a method for obtaining a plant having increased seed size, said method comprising the steps consisting of:
a) transforming at least one plant cell or plant tissue by means of at least a vector as defined previously;
b) cultivating the cell(s) or plant tissue thus transformed so as to generate a plant containing in its genome at least an expression cassette according to the invention, whereby said plant has increased seed size.

According to the invention, "increased seed size" means that the transformed plant have a seed bigger (larger) than a seed from a wild type plant (non-transformed plant). Such an increase in seed size is desirable to increase seed and or endosperm yield and to improve the germination and vigour of seedlings.

The invention also relates to a method for increasing plant growth rate, said method comprising the steps consisting of:
a) transforming at least a plant cell or plant tissue by means of at least a vector as defined previously;
b) cultivating the cell(s) or plant tissue thus transformed so as to generate a plant containing in its genome at least an expression cassette according to the invention.

Plant growth rate can be increased with either an improvement in final yield or earlier flowering and harvest.

The invention also relates to a method for obtaining a plant having decreased seed moisture content, said method comprising the steps consisting of
a) transforming at least a plant cell or plant tissue by means of at least a vector as defined previously;
b) cultivating the cell(s) or plant tissue thus transformed so as to generate a plant containing in its genome at least an expression cassette according to the invention, whereby said plant has decreased seed moisture content.

The over-expression of the EMP4 gene into the endosperm (with the aim of an endosperm promoter) increases the speed of the seed development leading to a seed having a lower moisture content than a normal seed (wild type) at harvest.

This is of interest and useful for reducing drying costs.

The invention also relates to a method for increasing plant starch and proteins accumulation, said method comprising the steps consisting of:
a) transforming at least a plant cell or plant tissue by means of at least a vector as defined previously;
b) cultivating the cell(s) or plant tissue thus transformed so as to generate a plant containing in its genome at least an expression cassette according to the invention, whereby said plant has increased starch and proteins content.

The invention also relates to a method for increasing grain filling, said method comprising the steps consisting of:
a) transforming at least a plant cell or plant tissue by means of at least a vector as defined previously;
b) cultivating the cell(s) or plant tissue thus transformed so as to generate a plant containing in its genome at least an expression cassette according to the invention.

The invention also relates to a method for speeding seed development, said method comprising the steps consisting of:
a) transforming at least a plant cell or plant tissue by means of at least a vector as defined previously;
b) cultivating the cell(s) or plant tissue thus transformed so as to generate a plant containing in its genome at least an expression cassette according to the invention.

The transformation of vegetable cells can be achieved by any one of the techniques known to one skilled in the art.

It is possible to cite in particular the methods of direct transfer of genes such as direct micro-injection into plant embryoids (Neuhaus et coll. 1997), vacuum infiltration (Bechtold at al. 1993) or electroporation (Chupeau et coll., 1989) or direct precipitation by means of PEG (Schocher et coll., 1986) or the bombardment by gun of particules covered with the plasmidic DNA of interest (Fromm M et al., 1990).

It is also possible to infect the plant with a bacterial strain, in particular *Agrobacterium*. According to one embodiment of the method of the invention, the vegetable cells are transformed by a vector according to the invention, the said cell host being able to infect the said vegetable cells by allowing the integration, in the genome of the latter, of the nucleotide sequences of interest initially contained in the above-mentioned vector genome. Advantageously, the above-mentioned cell host used is *Agrobacterium tumefaciens*, in particular according to the method described in the article by An et al., (1986), or *Agrobacterium rhizogene*, in particular according to the method described in the article by Guerche et al. (1987).

For example, the transformation of vegetable cells can be achieved by the transfer of the T region of the tumour-inducing extra-chromosome circular plasmid of *Agrobacterium tumefaciens*, using a binary system (Watson et al., 1994). To do this, two vectors are constructed. In one of these vectors the T region has been eliminated by deletion, with exception of the right and left borders, a marker gene being inserted between them to allow selection in the plant cells. The other partner of the binary system is an auxiliary plasmid Ti, a modified plasmid which no longer has any T region but still contains the virulence genes vir necessary to the transformation of the vegetable cell.

According to a preferred mode, it is possible to use the method described by Ishida et al. (1996) for the transformation of Monocotyledons.

According to another protocol, the transformation is achieved according to the method described by Finer et al. (1992) using the tungsten or gold particle gun.

Selection:

The engineered plant material may be selected or screened for transformants (those that have incorporated or integrated the introduced nucleotide construction(s)). Such selection and screening methodologies are well known to those skilled in the art. The selection and screening method is chosen depending on the marker gene used.

An isolated transformant may then be regenerated into a plant.

Regeneration:

Normally, regeneration is involved in obtaining a whole plant from the transformation process. The term "regeneration" as used herein, means growing a whole plant cell, a group of plant cells, a plant part or a plant piece (for example, from a protoplast, callus, or tissue part).

Methods of regenerating whole plants from plant cells are known in the art, and the method of obtaining transformed and regenerated plants is not critical to this invention.

In general, transformed plant cells are cultured in an appropriate medium, which may contain selective agents such as antibiotics, where selectable markers are used to facilitate identification, of transformed plant cells. Once callus forms, shoot formation can be encouraged by employing appropriate plant hormones in accordance with known methods and shoots transferred to rooting medium for regeneration of plants. The plants may then be used to establish repetitive generations, either from seeds or using vegetative propagation techniques.

The invention also concerns the use of the transgenic plants obtained according to the invention, or parts of these plants, in particular seeds, grains, and fruits for preparing derived products, in particular food products.

The products obtained, whether it be seeds with a higher oil content, flours of seeds or grains with a higher starch, protein or oil content, also come within the scope of the invention.

The invention also provides any composition for human or animal food prepared from the said obtained products.

The present invention also relates to a method for reducing organs development and particularly for reducing internodes length, said method consisting of obtaining a maize plant having reduced internodes length as compared to a wild type plant, comprising the step consisting of inhibiting the expression of a protein having at least 80% identity with SEQ ID No 2 within a maize plant, thus obtaining a plant having reduced internodes length as compared to a plant where the expression of SEQ ID No 2 is not inhibited.

A tissue-specific repression of the EMP4 gene is obtained by inhibition of the EMP4 gene using methods known in the art, as RNAi and antisens technology. Any other method known by the man skilled in the art is also useful.

The EMP4 gene could be repressed specifically in the internodes or in the stem by using specific promoters of these organs. In this case for example, the EMP4 gene is placed in the antisense orientation and is operatively linked to a promoter specific of the stem or of the internodes.

In addition to the use of the invention to create improved plants via plant modification via transgenesis the invention can be used to develop molecular markers to screen for favourable EMP4 alleles in the plant of interest. Particular EMP4 alleles may be linked to desirable agronomic characteristics such as plant growth rate, stature and yield.

The present invention will be further understood in view of the annexed figures and following examples.

DEFINITIONS emp4 means the emp4 plant mutant, either homozygous or heterozygous for the mutation (plants containing an EMP4 mutated gene).

emp4/+ and +/emp4 mean plants heterozygous for the emp4 mutation (1 mutated copy of the EMP4 gene).

emp4/emp4 means plants homozygous for the emp4 mutation (2 mutated copies of the EMP4 gene).

+/+ means wild type plants.

Sequence Listing:

SEQ ID No: 1: Maize EMP4 cDNA sequence.
SEQ ID No: 2: Maize EMP4 amino acid sequence.
SEQ ID No: 3: Maize EMP4 genomic sequence.
SEQ ID No: 4: Rice EMP4 cDNA sequence.
SEQ ID No: 5: Rice EMP4 amino acid sequence.
SEQ ID No: 6: Rice EMP4 genomic sequence.
SEQ ID No: 7: Maize EST BQ164351.
SEQ ID No: 28: Consensus sequence between SEQ ID No: 2 and SEQ ID No: 5.
SEQ ID No: 32: Maize BETL9 promoter sequence (pBETL9).

TABLE 1

EMP4 oligonucleotide primers and probes used in the following examples:

| Primer/Probe Name | SEQ ID No: | Primer region | Sequence 5'→3' |
|---|---|---|---|
| Probe1 | SEQ ID No. 8 | | |
| Oest2 | SEQ ID No: 9 | 1118 to 1137 of maize EMP4 cDNA (forward oligonucleotide) | TGATGGAGAGGATGCGGGAG |
| Oest3 | SEQ ID No: 10 | 1300 to 1320 of maize EMP4 cDNA (reverse oligonucleotide) | TGCCTCAATCAGCAAACCCTG |
| Oest5 | SEQ ID No: 11 | 1112 to 1147 of maize EMP4 cDNA (forward oligonuoleotide) | TGGAGAGGATGCGGGAGTGCCGGTGTC |
| Oest7 | SEQ ID No: 12 | 1172 to 1198 of maize EMP4 cDNA (forward oligonucleotide) | TGGTGATTCGGTTGGCCTGCAGGCTTG |

TABLE 1-continued

EMP4 oligonucleotide primers and probes used in the following examples:

| Primer/Probe Name | SEQ ID No: | Primer region | Sequence 5'→3' |
|---|---|---|---|
| Oest7rev | SEQ ID No: 13 | 1172 to 1198 of maize EMP4 cDNA (reverse oligonucleotide) | CAAGCCTGCAGGCCAACCGAATCACCA |
| RT5 | SEQ ID No: 14 | 294 to 313 of maize EMP4 cDNA (forward oligonucleotide) | GCACTTCTTCCACTGGTGCT |
| RT5rev | SEQ ID No: 15 | 294 to 316 of maize EMP4 cDNA (reverse oligonucleotide) | GGGAGCACCAGTGGAAGAAGTGC |
| ZmH2B 5for | SEQ ID No: 16 | | ATGGCGCCCAAGGCGGAGAAGAAGC |
| ZmH2B 5rev | SEQ ID No: 17 | | CGAGGTGAACTTGGTGACGGC |
| | SEQ ID No: 18 | | GAGGGCTGTACATTCTGGGA |
| | SEQ ID No: 19 | | TCCTGATCAGTCACGCTGTC |
| OmuA | SEQ ID No: 20 | | CTTCGTCCATAATGGCAATTATCTC |
| CP1 | SEQ ID No: 21 | | AGCTGCTCCTTCTTCTCGTG |
| TSP1 | SEQ ID No: 22 | | GCACTTCTTCCACTGGTGCT |
| EMP4For | SEQ ID No: 23 | | ATGGATCCGACATGTGCATCTCAGTCCGCCACGGG |
| EMP4Rev | SEQ ID No: 24 | | CAATGAATTCTATTTCAATTAGCCGG |
| pMRP1for | SEQ ID No: 25 | | GGGTACCTCGAGATGCATGTATTAATTCATTGACACC |
| pMRP1rev | SEQ ID No: 26 | | GGAAGCTTGCGAGGGGTTAAGTACTACACAAGTTG |
| Mu3 specific probe | SEQ ID No: 27 | | |
| pBETL9 forXho | SEQ ID No: 29 | | CCCTCGAGTTACTCATGATGGTCATCTAGG |
| pBETL9 revXba | SEQ ID No:30 | | GCTCTAGAGGGTATAACTTCAACTGTTGACGG |
| EMP4For2 | SEQ ID No: 31 | | GCATGTGCATCTCAGTCCGC |

Scale bars: 5 mm in B and C, 1 mm in D, 5 cm in E.

Figure 2:
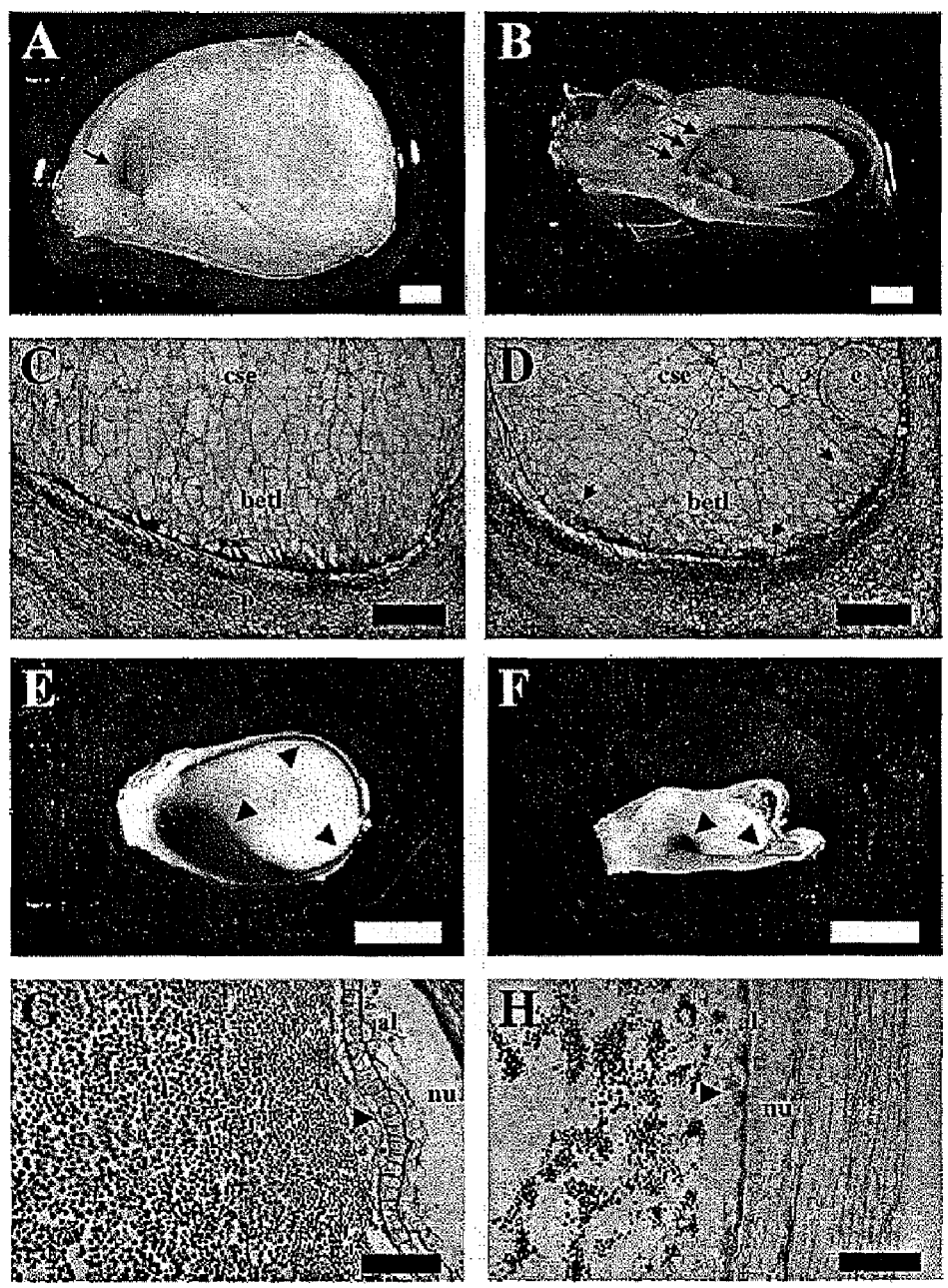

FIG. 2: Effect of maize emp4 mutation on basal transfer layer and aleurone.

(A-D) Longitudinally section of 14 DAP wild-type (A and C) and mutant (B and D) kernels carrying the pBETL1-GUS transgene and showing GUS precipitate in basal endosperm transfer layer cells. (E-H) Longitudinally section of 20 DAP wild-type (E and G) and emp4 (F and H) kernels carrying the pVP1-GUS transgene and showing GUS precipitate in embryo and aleurone cells.

C, D, G and H are 10 μm wax sections stained with PAS.

Scale bars: 1 mm in A, B; 200 μm in C, D; 2 mm in E, F; 100 μm in G, H. Arrows and arrowheads highlight areas of interest.

al, aleurone; betl, basal endosperm transfer layer; cse, central starchy endosperm;

e, embryo; esr, embryo surrounding region; nu, nucelus; p, placento-chalazal region.

Figure 3:
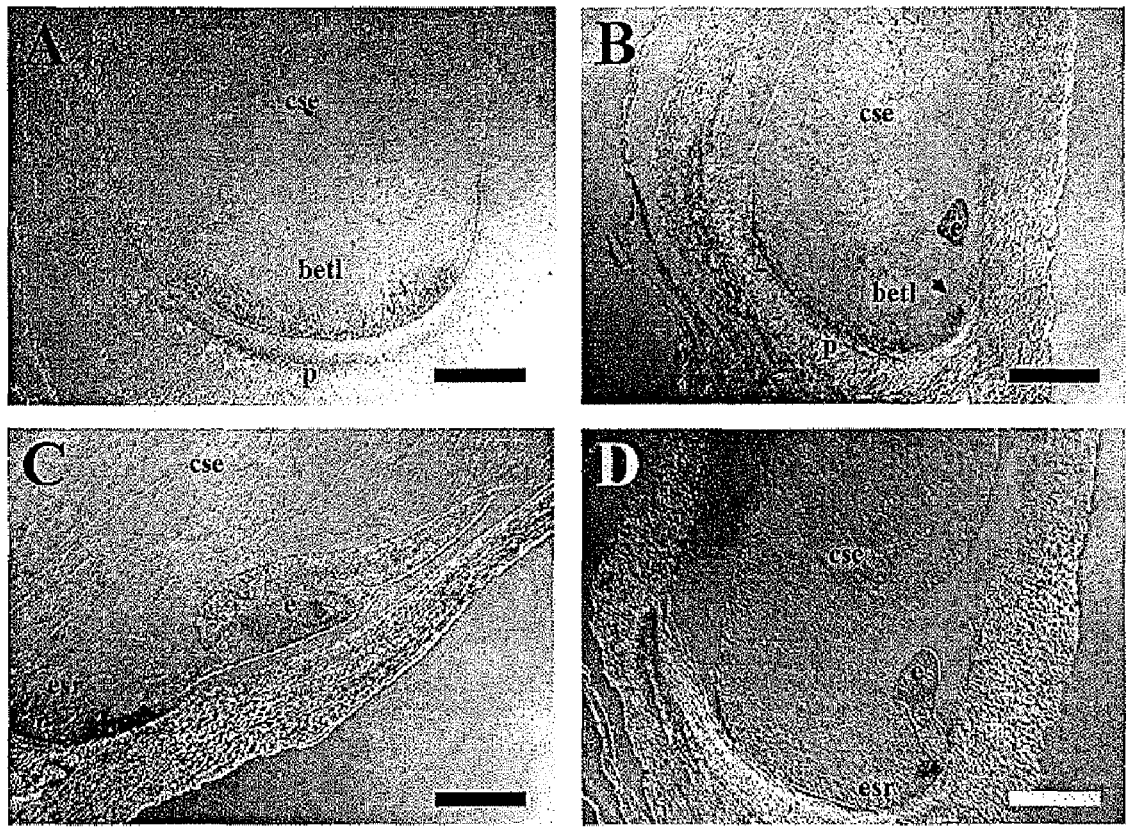

FIG. 3: Effect of maize emp4 mutation on basal endosperm gene expression.

mRNA in situ analysis in wild-type (A and C) and mutant (B and D) kernels at 11 DAP with ZmMeg1 antisense probe (A and B) and with ZmEsr2 antisense probe (C and D).

Scale bar: 500 μm.

betl, basal endosperm transfer layer; cse, central starchy endosperm; e, embryo; esr, embryo surrounding region; p, placento-chalazal region.

Figure 4:
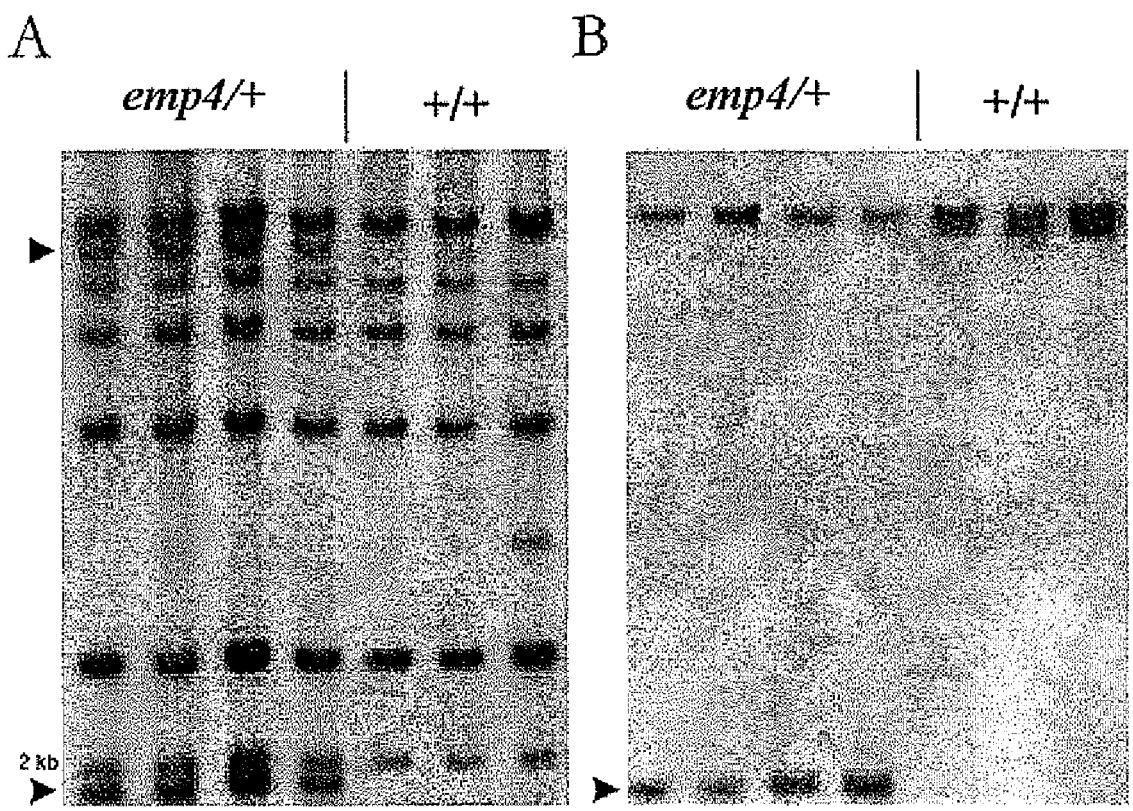

FIG. 4: DNA gel blot analyses of a Mu3 element linked to emp4 mutation.

(A) A Mu3 transposon-tagged PstI fragment (arrows) cosegregating with the emp4 mutation.

(B) DNA blot hybridized with probe1. The blots identified a 2 Kb PstI band and an 11.2 kb BamHI band co-segregating with the emp4 mutation (arrows).

Figure 5:
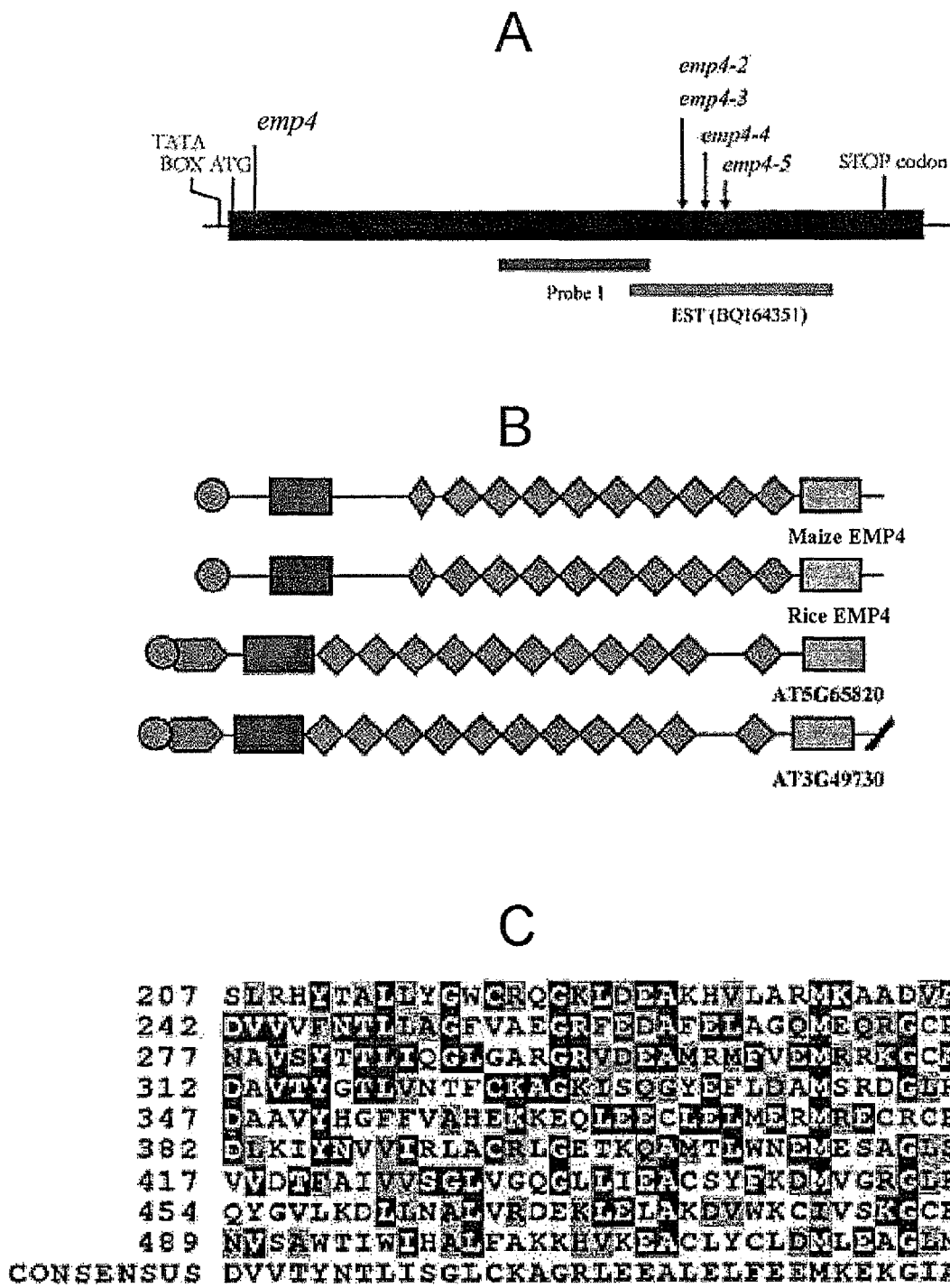

FIG. 5: Organization of EMP4 gene and protein structure.

(A) Schematic diagram of the EMP4 gene. The location of the Mu3 transposon insertion of emp4mutant in the maize coding sequence and position of Mutator insertions of known emp4 mutants is indicated with arrows. Putative TATA box, ATG transcriptional start site and Stop codon are shown. Genomic regions comprising Probe 1 and EST clone BQ164351 are indicated.

(B) Schematic alignments of maize EMP4, rice EMP4 and Arabidopsis AT3g49730 and AT5g65820 predicted aminoacid products. The PPR motifs and the PLS motif are indicated in green rhomboids. The putative signal peptide is indicated as brown circles. The novel N-terminal and C-terminal domains are indicated as blue and green boxes, respectively.

(C) Comparison of the nine PPR motifs found in EMP4 (SEQ ID No: 2, amino acids 207-523) with the PPR consensus sequence (SEQ ID No: 33). Residues identical to the consensus are shaded in black, and similar residues are shaded in gray.

(D) Alignment of the novel EMP4 C-terminal domain present in maize EMP4 (SEQ ID No: 2, amino acids 538-590), rice EMP4 (AC135956) (SEQ ID No: 5, amino acids 553-606), and *Arabidopsis* AT3g49730 (SEQ ID No: 34) and AT5g65820 (SEQ ID No: 35).

(E) *Agrobacterium*-mediated transient expression in tobacco leaf epidermal cells of EMP4-GFP. GFP fluorescence was visualized using a confocal microscope.

Figure 6:
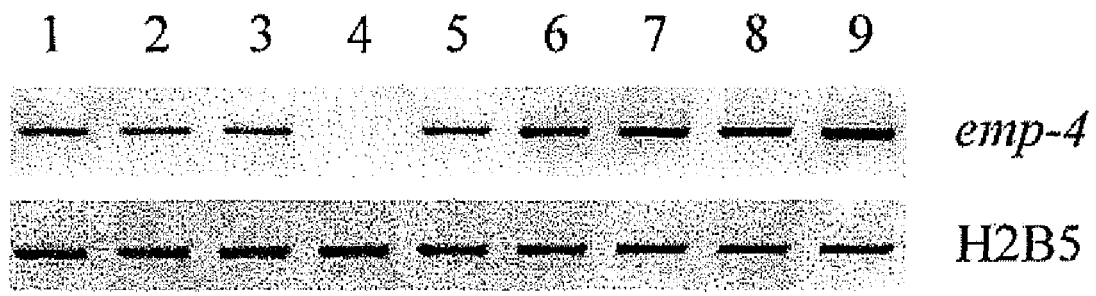

FIG. 6: Maize EMP4 gene is expressed in all vegetative and most reproductive tissues.

RNA was isolated from leaves, roots and stems (lane 1, 2, 3), anthers (lane 4), ovaries (lane 5), 6 DAP embryo and endosperm (lane 6 and 7), and 12 DAP embryo and endosperm (lane 8 and 9). RT-PCR products were detected using EMP4 gene specific primers Oest2 and Oest3 (top gel) (see Table1) and a histone2-specific primers (bottom gel).

Figure 7:
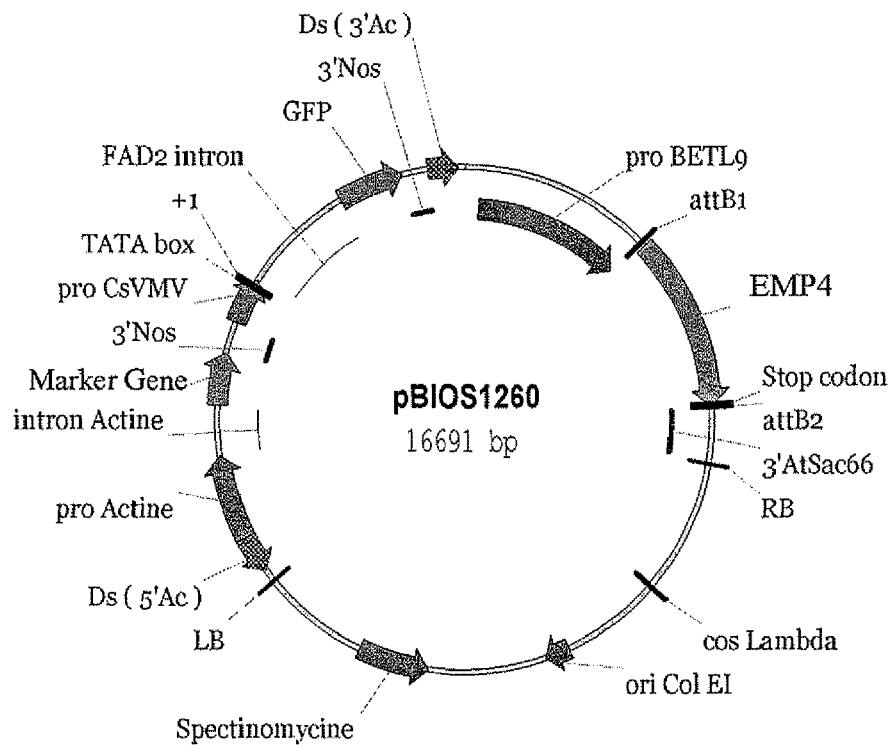

FIG. 7: Construct comprising the EMP4 gene under transcriptional control of the pBETL9 promoter.

Figure 8:
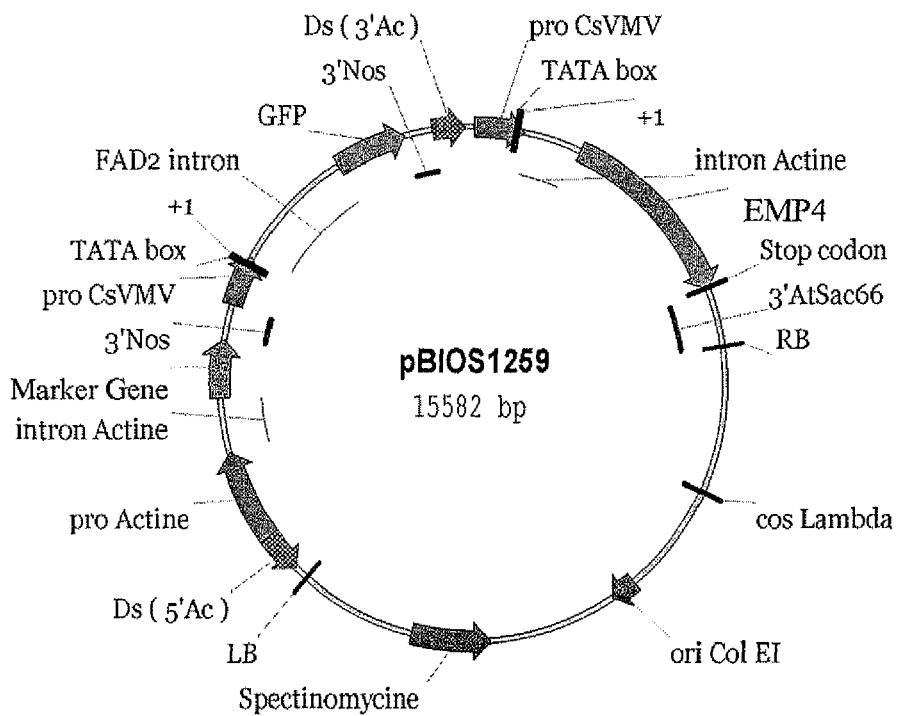

FIG. 8: Construct comprising the EMP4 gene under transcriptional control of the pCsVMV promoter.

EXAMPLES

The invention will now be described by the way of the following examples, which should not be construed as in any way limiting the scope of the invention.

Example 1

Phenotypic and Genetic Characterization of the Maize emp4 Mutation

The emp (empty pericarp) phenotype represents a class of defective-kernel mutants with a severe reduction in endosperm development. Mutant seeds, recovered in the selfed progeny of a +/emp plant, appear reduced in size, devoid of endosperm material, and flattened by compression of surrounding normal kernels.

Mutant Isolation and Propagation

The maize emp4 mutation (see FIG. 5A) has been isolated in the F2 of a cross between a maize Mutator line and a maize inbred line. This F2 progeny segregated for normal and defective seeds in a 3:1 ratio thus showing that the mutant emp4 behaves as a monogenic recessive.

Because the emp4 mutation is a seed lethal mutation, it has been maintained in heterozygosis and propagated by out-crossing +/emp4 plants to different maize inbred lines (A188, W64A, H99).

The maize emp4 mutation was mapped onto chromosome 1 L after crossing heterozygous mutant plants to the whole set of B-A translocations.

Figure 1:
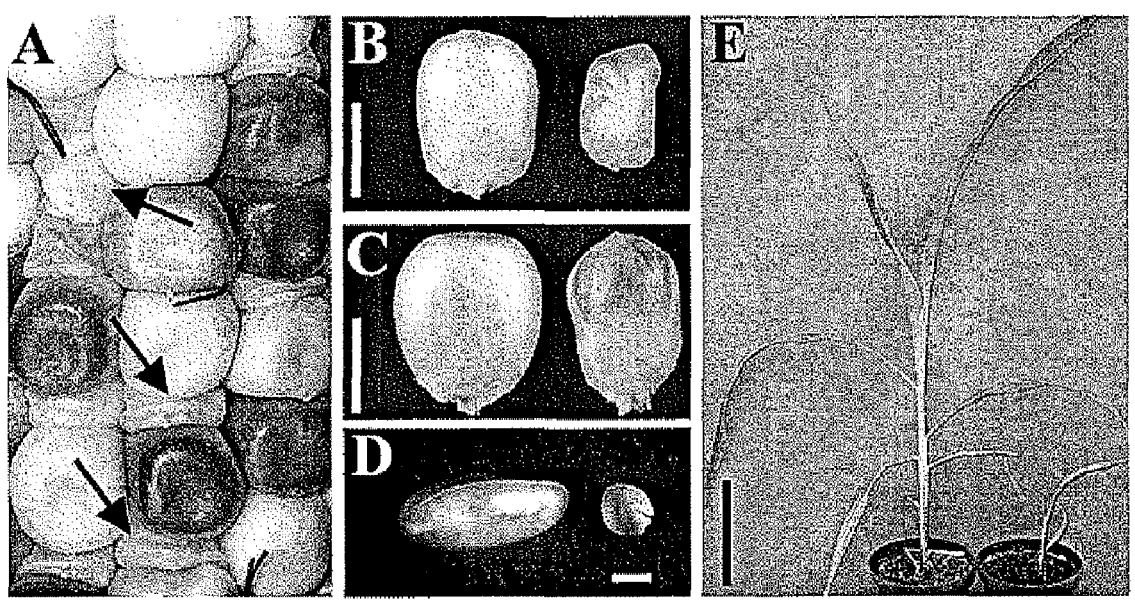
FIG. 1: Maize mutant emp4 seed and plant phenotypes.
(A) Ear segregating for wild-type and emp4 mutant kernels (arrows).
(B) 20 DAP wild-type (left) and mutant (right) kernels.
(C) 30 DAP wild-type (left) and mutant (right) kernels.
(D) Isolated 20 DAP wild-type (left) and mutant (right) embryos.
(E) Comparison of wild type (left) and homozygous emp4 mutant (right) plants obtained from 30 DAP rescued and cultured embryos.

Mutants are recognizable as early as 12 DAP, because of a pale, translucent and collapsed appearance of the caryopsis (FIG. 1A). Comparison of wild-type and mutant sibling kernels at 20 and 30 DAP shows a reduction in size of the mutant caryopsis (FIGS. 1B and C), whereas the pericarp, being a maternal tissue, is not reduced in size (normal size). At 20 DAP, emp4/emp4 embryos already appear much smaller compared to wild-type siblings (FIG. 1D), at maturity homozygous emp4 seeds are lethal and do not germinate. However 30 DAP explanted emp4 embryos could be rescued by cultivating on a basal medium, then transferring seedlings to soil. For embryo rescue experiments, immature embryos were excised from the caryopsis and cultivated on a synthetic medium as described in Consonni et al. (2003). Embryo-rescue seedlings at three leaf stages were transferred to soil and, after a period of acclimatization, they were grown in pots, under standard greenhouse conditions.

Although not significantly altered in their vegetative architecture, homozygous mutant plants exhibited delayed growth (FIG. 1E), but were able to reach reproductive maturity.

Thus the EMP4 gene is required for normal plant development, though the effect of the emp4 mutation appears to be particularly severe on endosperm development. EMP4 gene plays an essential, non-redundant role during the entire plant life cycle.

Example 2

Endosperm Domains Morphology are Altered in Maize emp4 Mutant Kernels

The effect of the mutation on endosperm domain specification and morphology has been studied by using two approaches, i.e. GUS staining and in situ hybridization with specific markers.

Example 2.1

Gus Marker Analysis

VP1 promoter transcriptional fusion to β-glucuronidase (GUS) (Costa et al., 2003) and BETL1 promoter transcriptional fusion (Hueros et al., 1999b) were introgressed in a maize A188 inbred background for 3 generations.

These maize transgenic lines were crossed to emp4/+ and F1 plants were genotyped for the presence of β-glucuronidase (GUS) by PCR using GUS-specific oligonucleotides (Gutierrez-Marcos et al., 2004), and backcrossed to emp4/+ plants.

Kernels were cut longitudinally and GUS was detected histochemically according to the methods previously described in Costa et al., (2003) and Gutierrez-Marcos et al., (2004). Wax sections were mounted onto BDH slides and counterstained with Periodic Acid Schiff's (PAS) Reagent. Polysaccharides stain purple-red.

pVP1-GUS plants were introgressed into the emp4 background, thus enabling GUS detection of the embryo and aleurone layers. GUS staining was performed on longitudinally-cut-hand sections of 20 DAP wild-type and mutant kernels (FIGS. 2E and 2F). In wild-type seeds, GUS staining was present throughout the aleurone, extending from the germinal to abgerminal face of the seed (FIG. 2E), whereas GUS staining was detected only in the germinal face of mutant seeds (FIG. 2F). Wild-type aleurone usually appeared as a single layer of isodiametric cells (FIG. 2G) whereas in mutants, it was discontinuous and contained many irregularly shaped cells (FIG. 2H). Interestingly, by using pVP1-GUS reporter, the presence of ectopic GUS staining was noted in discrete portions of the basal endosperm.

In the maize endosperm, the cells at the chalazal pole are committed to develop into transfer cells and form a specific region named the BETL (Basal Endosperm Transfer Layer), presumably involved in nutrient transport from the maternal phloem to the endosperm. To ascertain whether the emp4 mutation has an effect on the development of this region, pBETL1-GUS mutant and wild-type seeds were obtained after introgression of the reporter line into the emp4 background.

Mutant and wild-type maize sibling seeds were analyzed after staining for GUS (FIGS. 2A, 2B, 2C and 2D). In wild-type seeds, expression of the transgene was confined to the BETL (FIG. 2A), where it was evenly distributed in two or three adjacent cell layers of the transfer region, decreasing progressively toward the center of the endosperm (FIG. 2C). By contrast, reporter gene expression was irregular in mutant seeds (FIG. 2B) and GUS staining was often observed in the peripheral-most cells of the basal endosperm (FIG. 2D), if at all present. In addition, we noticed that some sectors of the emp4 basal endosperm were also devoid of cell wall ingrowths in emp4 endosperms, when compared to wild-type siblings (FIGS. 2C and D).

These data indicate that the emp4 mutation mainly affects BETL domain that appears only partially and irregularly developed. Defects in the BETL is correlated with reduced rates of grain filling (Maitz et al., 2000), which in some cases leads to seed abortion as observed in emp4 mutants.

Sections were counterstained with PAS, which allowed also to qualitatively compare starch and carbohydrate composition in mutant and sibling wild-type kernels. Starch accumulation was notably reduced in the central starchy endosperm (CSE) of emp4 mutants when compared to their wild-type siblings (FIGS. 2H and G).

Example 2.2

In Situ Hybridization with Specific Markers mRNA in situ hybridisation analysis was performed at 11 DAP (Days After Pollination) according to Costa et al., (2003) to determine the expression of Zm-Meg1 and Esr genes, as specific markers for respectively Basal Endosperm Transfer Layer (BETL) and Embryo Surrounding Region (ESR).

Kernels were trimmed along the medial-lateral axis and immediately fixed in ice-cold FAA, dehydrated in an ethanol series, and embedded in wax. Sections were cut at 10-12 μm and affixed onto pre-treated Superfrost Plus slides (BDH). Riboprobes were labelled using the DIG RNA labeling mix (Boehringer Mannheim, catalogue number 1175025) according to manufacturer's instructions, and slides were hybridised overnight at 50° C. Slides were viewed with a Zeiss AxioPhot microscope under DIC3-5 optics and images were digitally recorded.

mRNA in situ hybridization analysis were carried on sections of 11 DAP emp4 and wild-type kernels using an antisense ZmMeg1 probe (Gutierrez-Marcos et al., 2004) to detect BETL-specific ZmMeg1 transcript. ZmMeg1 transcript was uniformly distributed throughout the BETL of wild-type kernels (FIG. 3A). In contrast, ZmMeg1 transcript was irregularly distributed and limited to small sectors of emp4 basal endosperms (FIG. 3B).

A ZmEsr2 antisense probe has been used to detect all three Esr-specific transcripts (ZmEsr1, ZmEsr2 and ZmEsr3) (Opsahl-Ferstad et al., 1997). No differences were detected in wild-type and sibling emp4 kernels, as in both instances ZmEsr transcripts were confined to the ESR (FIGS. 3C and D).

Together the results from in situs and crosses with GUS lines suggest that the emp4 mutation affects the correct development of the BETL and aleurone cell layers. It is possible that the metabolic activity of the BETL region in the syncitial endosperm phase is important in the differentiation of this region into BETL cells. Since the activity of the BETL layer is critical for importation of nutrients into the endosperm it is expected that a malformed BETL layer will lead to a defective endosperm and impact on aleurone differentiation and starchy endosperm cell number.

Example 3

Co-Segregation Analysis and Molecular Characterization of the Maize emp4 Mutation Since the emp4 mutation was isolated in an active Mutator (Mu) population, cosegregation analysis was performed aiming at the identification of the gene. Plants bearing the mutation were outcrossed to W64A, a low Mutator copy number maize inbred line, to facilitate the molecular analysis and the F1 plants were selfed to obtain segregating families. DNA extracted from leaves of +/emp4 and +/+ single individuals, whose genotype has been ascertained by selfing was compared by Southern analysis.

DNA Gel Blot Analysis

For cosegregation analysis, maize genomic DNA was extracted from 7-days old seedlings and leaf tissues, using the urea extraction method known in the art. For DNA gel blots 10 ug of digested genomic DNA was separated on 0.8% agarose gels. DNA fragments were transferred to Hybond N+ membranes (Amersham Biosciences) with 10× SSC. Membranes were subsequently probed with $\alpha^{32}$P-labeled probes prepared from gel-purified restriction fragments labeled by random primer extension (Prime-a-gene labeling system; Promega, Madison, Wis.).

Hybridization probes were as follows: Mutator3 (Mu3) specific probe (SEQ ID No: 27) corresponds to the internal HindIII-XbaI Mu3 cloned fragment. Probe1 (SEQ ID No: 8) was obtained from the Mu-tagged genomic clone, and corresponds to a 401 bp PstII-Mlu1 restriction fragment of the genomic DNA flanking Mu3 insertion.

Genomic DNA extracted from leaves of +/emp4 and +/+ individuals whose genotype had been ascertained by selfing, was compared by Southern blot analysis. Genomic DNA was digested with PstI, a methylation-sensitive endonuclease that cuts once inside the Mu3 element. Hybridization with a Mu3-specific probe revealed two fragments of approximately 9 kb and 2 kb in length cosegregating with the mutant phenotype (FIG. 4A).

Subsequent hybridization with a different Mu3 probe revealed that the 5' end of the Mu3 element was included in the 2 kb fragment.

A 11.2 kb polymorphic fragment linked to emp4 was observed also in BamH1digest. The same polymorphisms were detected in homozygous emp4 plants obtained from embryo rescue.

Cloning of the Genomic Fragments

A subgenomic library of the polymorphic Mu3 fragment was prepared with DNA extracted from emp4/+plants in the pBSSK vector according to manufacturer's instructions (Stratagene, La Jolla, Calif.). By screening this library with a Mu3-specific probe, a single hybridizing clone was isolated and the presence of a Mu3 element and DNA flanking the insertion were determined after sequencing.

The 2 kb Mu3-hybridising PstI restriction fragment was cloned from a sub genomic library prepared from size-fractionated PstI fragments of emp4/+DNA. The cloned DNA comprises 1115 bp of genomic sequence flanking the Mu3 insertion and was mapped to the long arm chromosome one, between markers UMC140 and UMC106. To verify the identity of the cloned DNA, a 401 bp PstI-Mlu1 sequence (probe 1) was used tore-probe the same PstI digested Southern gel blot.

In emp4/+individuals, the same 2 kb PstI fragment and an additional 11 kb fragment corresponding to the W64A EMP4 wild-type allele, were identified (FIG. 4B). In wild type, the same 11 kb W64A band was identified, plus a second 10 kb RFLP (Restriction Fragment Length Polymorphism) band, corresponding to the Mutator line wild type allele (FIG. 4B). Co-segregation analysis was performed on a total of 100 plants including individuals from $F_1$ and $F_2$ segregating families and the data obtained were concordant, indicating that the Mu3 element was inserted either in the EMP4 gene itself or in a closely linked locus. Southern blot analysis on a wide range of inbred lines indicated that EMP4 is a single copy gene in maize.

The EMP4 Pst1-Mlu1 probe1 fragment was genetically mapped by RFLP (Restriction Fragment Length Polymorphism) using the LHRF population (Lignées Hautement Recombinantes F2 X F252; Highly Recombinant Inbred Lines F2 X F252). Mapping data were analysed with the mapmaker/EXP3.0 software (Lander et al., 1987) with RiSib and Kosambi centiMorgans parameters. This mapping positioned the maize EMP4 gene on chromosome 1L, between UMC140 and UMC106. All these data indicate that the Mu3 element was inserted either in the EMP4 gene itself or in a tightly linked locus.

A reverse genetics approach was adopted to verify the identity between the cloned sequence and the EMP4 gene. To this end, oligonucleotide primers corresponding to the genomic sequence were employed in combination with Mu transposon-specific primers for a survey in a 'Mutator gene machine'. This Mutator gene machine is a collection of 27,500 plants in which endogeneous Mu elements have been allowed to transpose at high frequency. Screening for Mu insertions in EMP4 was performed on F1 plant material and confirmed for their germinal status on F2 plant materials. Mutant screens were performed using a PCR-based method with an efficient TIR specific primer SEQ ID No: 20 (OmuA) which hybridizes with both the 5' and the 3'TIR and two EMP4 specific primers, SEQ ID No: 21 (CP1) and SEQ ID No: 22 (TSP1). Four independent germinal Mu insertions were identified each having a phenotype similar to maize emp4. Complementation analyses of emp4 heterozygous plants with plants bearing the new insertions reveals, in all four cases, that the newly identified Mu insertions define mutations that are allelic to emp4. The new mutants were named E2439 (emp4-2), C1220 (emp4-3), C232 (emp4-4) and B2023 (emp4-5) (FIG. 5A). These data indicate that the 1115 bp cloned genomic sequence contains a portion of the EMP4 gene.

Example 4

Maize EMP4 Gene is Predicted to Encode a Mitochondria-Targeted Pentatricopeptide-Repeats Containing Protein In order to identify the complete sequence of the maize EMP4 gene the genomic fragment was used to in an EST database search using BLASTN. This resulted in the identification of an EST (BQ164351) (SEQ ID No: 7) from *Zea mays* immature ears which aligned with 100% homology over a region of overlap of 75 bp.

Gene specific primers were designed and used in rapid amplification of cDNA ends (RACE) to generate full-length wild-type EMP4 cDNA. To this aim poly(A$^+$) RNA was prepared from immature ears. Total RNAs was extracted from maize tissues ground under liquid $N_2$ as previously described and poly(A)$^+$RNA was selected by means of the Oligotex kit, (Quiagen, Hilden, Germany) and following the manufacturer instructions. Reverse transcription and rapid amplification of cDNA ends were performed according to the recommended protocol provided by the SMART™ RACE cDNA Amplification kit (BD Biosciences Clontech, Palo Alto, Calif.). Reaction for the 3'RACE were conducted with the primer Oest5 and nested primer Oest7 both designed on the EST BQ164351 sequence. For the 5'GRACE the universal primer provided by the kit was used in combination with primer Oest7rev, and with the nested primer RT5rev. The internal cDNA portion was generated by RT-PCR with the following set of primers: RT5 forward primer derived from the genomic clone sequence, and Oest3 reverse primer derived from the EST sequence. The Oest7rev and Oest3 primers were designed on the EST BQ164351 sequence whereas RT5 and RT5rev sequence was deduced from the portion of the genomic clone overlapping with the 5' RACE product. These amplifications showed that the 5' RACE, internal and 3'RACE products were derived from the same cDNA.

In order to obtain the complete genomic sequence of EMP4, the maize Bacterial Artificial Chromosome (BAC) library ZmF2 (O'Sullivan et al., 2001) was screened with the EMP4 PstI-MluI 401 bp probe after labelling using ($\alpha^{32}$P-dCTP (Megaprime DNA labelling system, Amersham). The library filters were pre-hybridized for 5 hours in hybridization buffer (PerfectHyb Plus, SIGMA, St. Louis, Mo.) at 68° C. Hybridization was performed overnight. Filters were washed twice for 20 min in 2×SSC, 0.1% SDS and twice for 20 min in 0.2×SSC, 0.1% SDS. Hybridizing BACs were identified after 24 hour exposure with a Storm 860 Imaging System (Amersham, Buckinghamshire, UK).

3 identical hybridising BACs were isolated and a 5.2 kb region encompassing EMP4 was subcloned and directly sequenced. The aligned genomic and cDNA sequences show complete homology and allow the determination of the gene structure. The EMP4 gene contains a single exon and a putative TATA box in position −38 (FIG. 5A). The full length maize EMP4 cDNA is 1950 bp (SEQ ID No: 1), excluding the poly-A tail and the maize EMP4 predicted protein contains an open reading frame of 614 amino acids (aa) (SEQ ID No: 2).

The putative ORF was used in a Pfam search to identify any conserved internal domains. This analysis revealed that EMP4 encodes a PPR protein, showing high homology to one rice and two *Arabidopsis* pentatricopeptide repeat (PPR) proteins (FIG. 5B). A region of the EMP4 protein extending from residue 209 to residue 525 contains nine putative PPR motifs showing a variable degree of conservation (FIG. 5C). The PPR motifs are contiguous, except for motifs 7 and 8, which are interrupted by two amino acids. The position of the 9 PPR motifs was therefore shifted forward by two amino acids, to allow the alignment with the PPR consensus sequence (Lurin et al., 2004). In addition, a short sequence preceding the PPR-tandem repeat motifs was detected, showing significant homology with the 31 aa long PPR-like short (PLS) motif (Lurin et al., 2004). Two other domains were identified in EMP4 sequence, one being located at the N-terminus between residue 47 and residue 102, and the other at the C-terminus, located between aa 538 and aa 590. The C-terminus domain had only two matches in the Pfam database to *Arabidopsis* sequences AT3g49730 and AT5g65820, previously described by Lurin et al., (2004). To better characterize this domain an exhaustive search of the PlantGDB sequences has been performed, which identified strong conservation of EMP4 with a predicted protein in a rice BAC genomic sequence (AC135956). The alignment of the four C-terminus domains is shown in FIG. 5D and the domain organization of the corresponding proteins is shown in FIG. 5B. The domain organization of maize EMP4 and rice AC135956 is most similar (highly conserved), while the two *Arabidopsis* sequences contained an additional domain at the N-terminus, located between residues 1 and 61 in AT3g49730 and between residues 8 and 69 in AT5g65820 (FIG. 5B).

Further, a putative targeting signal peptide has been identified at the N-terminus of EMP4 and in the three homologous protein sequences using specific software. A chloroplast subcellular localization signal was predicted for EMP4 sequence and for rice AC135956, whereas a mitochondrial localization signal was predicted for AT3g49730 and AT5g65820 putative gene products. A program also predicted a chloroplast localization signal for EMP4 sequence, while no prediction was obtained for the other three protein sequences. To experimentally determine the subcellular localization of EMP4, we generated a translational EMP4-GFP fusion construct, and used this for transient expression studies in tobacco leaf epidermal cells. Confocal scanning laser microscopy analysis of leaf samples showed that the in vivo green fluorescence signal co-localized with mitochondria (FIG. 5E).

Example 5

Maize EMP4 Gene Expression Analysis

To compare the level of EMP4 transcript in different plant and seed tissues, semi-quantitative RT-PCR was performed using total RNA isolated from leaves, roots, stems, anthers, ovaries and immature embryos and endosperm.

First strand cDNA were synthesized from 5 ug of total RNA using an oligo d(T) primer following manufacturer's instructions.

For the semi-quantitative RT-PCR, two set of primers were used: the first comprises the EMP4 specific primers Oest2 and Oest3, the second set was designed on the sequence of the constitutively expressed histone gene H2B5, and used as control (ZmH2B5for and ZmH2B5rev). The amount of cDNA to be added to each reaction was determined on the basis of the product obtained with the control reaction. To detect transcript presence in different plant tissues, amplification conditions were as follows: 94° C. for 1 min, followed by 15 cycles of 94° C. for 30 sec, annealing at 58° C. for 20 sec, extension at 72° C. for 40 sec and final extension at 72° C. for 5 min. Products were analyzed on 2% TBE agarose gel and confirmed by hybridization. Specificity of the RT-PCR products was confirmed by sequence analysis.

Amplification with a set of specific primers for the orp-1 (orange pericarp-1) gene (Wright et al., 1992) was performed for each experiment to exclude DNA contamination in RNA samples. These primers (SEQ ID No: 18 and SEQ ID No: 19) are designed across an intron. The obtained products were of the size expected for cDNA amplification.

By using this procedure, transcripts were detected in all tissues analyzed except anthers. Higher levels are present in both embryo and endosperm at 6 and 12 DAP (FIG. 6). It was also been detected in leaves, roots, stems and ovaries.

Expression analysis was extended to the later stages of seed development (15 and 20 DAP). For the transcript level comparison the amplification conditions using primers Oest2 and Oest3 were as follows: 94° C. for 1 min, followed by 15 cycles (for histone) or 20 cycles (for EMP4) of 94° C. for 30 sec, annealing at 58° C. for 20 sec, extension at 72° C. for 40 sec and final extension at 72° C. for 5 min. Products were analyzed on 1.5% TBE agarose gel, stained with Vistra Green (Amersham Biosciences) and densitometrically analyzed using Typhon™ 9200 scanner and Image Quant Software. A threefold increase in EMP4 expression was observed at 20 DAP compared to 15 DAP (FIG. 6).

This data indicates that the EMP4 gene is transcriptionally active not only during seed development, where it is detected in both seed compartments, but in most plant tissues. However its transcript level is higher in the developing kernel compared to the vegetative tissues tested.

Example 6

EMP4 Cellular Localization Analysis

To generate a translation protein fusion between EMP4 and GFP (Green Fluorescent Protein), the full length ORF of the maize EMP4 (SEQ ID No: 1) was amplified by PCR and introduced in the binary vector pGWB5 by GATEWAY in vitro site-specific recombination (Invitrogen, Carslab, USA). This binary construct contains a CaMV 35S promoter that allowed the constitutive expression of the EMP4:GFP, and was introduced into *A. tumefaciens* strain GV3101 (pMP90) (Koncz and Schell, 1986) by electroporation.

*Agrobacterium tumefaciens* mediated transient expression was carried out in *Nicotiana tabacum* SR1 (cv Petit Havana). Briefly, a single colony of the transformed *Agrobacterium* was used to inoculate 5 ml of YEB medium, supplemented with 100 µg/mL kanamycin, 10 µg/ml gentamycin. The bacterial culture was incubated at 28° C. overnight and the bacteria were pelleted by centrifugation at 2200 g for 15 seconds in a microcentrifuge at room temperature. The pellet was washed three times with 1 ml of the infiltration buffer (50 mM Mes, pH 5.6, 2 mM $Na_3PO_4$, 0.5% glucose [w/v], and 100 µM acetosyringone) (Sigma, Poole, UK) and then resuspended in 1 ml of the same buffer. The bacterial suspension was diluted with infiltration buffer to adjust the inoculum concentration to 0.1 $OD_{600}$ value. The inoculum was delivered to the lamina tissues of tobacco leaves by gentle pressure infiltration through a small needle puncture created in the lower epidermis. The plant was incubated under normal growing conditions for 48 hours before confocal microscopy analysis. Leaf samples were harvested 48h after infiltration and protein fusions were visualized using a Zeiss LSM 510 META set to measure an emission band of 475 to 525 nm for GFP and an emission band of 599 nm for Mitotracker Red for mitochondrial colocalization. The software LSM dummy (Zeiss) was used for postacquisition image processing.

Example 7

Expression of the Maize EMP4 Gene in the BETL Region

The expression of the EMP4 gene increases during seed development and seems to be necessary for the correct differentiation and development of the BETL. Thus overexpression of EMP4 gene will lead to earlier differentiation of the BETL and to a BETL that is larger and more active in the importation of nutrients required for seed growth. Therefore EMP4 gene can be overexpressed using BETL-specific promoters, especially those which are active early in BETL development preferably before BETL cellularisation, in order to increase seed size and/or speed of seed development.

Example 7.1

Maize Transformation with ZmMRP1::EMP4 Construct

The coding region of the maize EMP4 gene (SEQ ID No: 1) was amplified from the EMP4 BAC using the primers EMP4For and EMP4Rev. The same amplification step is also possible by using the primers EMP4For2 and EMP4Rev. The PCR product was cloned into the vector pGEM-T-EASY (Promega) forming pBIOS1244 and the EMP4 sequence verified by DNA sequencing. The EMP4 coding region was then transferred as an NcoI (blunted), SpeI fragment into XmnI, XbaI-cut pENTR1A (Invitrogen) forming the plasmid pEMP4-Entr (also named pBIOS1245). The MRP1 promoter region (Gomez et al (2002)) is amplified from genomic maize DNA using the primers pMRP1for and pMRP1rev. The PCR product is cut with KpnI and HindIII and cloned into KpnI, HindIII-cut pBIOS664 forming pMRP1-R1R2Sac66pA. pBIOS664 is a pBluescript based plasmid that contains the CsVMV promoter (Verdaguer et al, 1996) fused to the rice actin 5'UTR (McElroy et al., 1991) and a terminator sequence derived from the *arabidopsis* Sac66 gene (Jenkins et al. (1999)). Between the promoter and terminator is the GATEWAY R1, R2 cassette (invitrogen). pMRP1-R1R2 Sac66pA is then transferred as an XhoI, PmeI fragment into the XhoI, PmeI cut plant binary plasmid pBIOS342 forming pMRP1R1R2 bin. (pBIOS342 is based on the binary vector pSB11(Komari et al (1996)) and contains a gene for selection of transformed plants). EMP4 is then fused to the MRP1 promoter by performing an LR clonase reaction between pEMP4-entr and pMRP1R1R2 bin. The resulting binary vector is then transferred to *agrobacterium* strain LB4404 (pSB1) according to Komari et al (1996). Maize cultivar A188 is transformed with these agrobacterial strains essentially as described by Ishida et al (1996).

Analysis of the transformed plants indicates that some plants overexpress EMP4 and this increased expression is earlier than normal in seed development. These plants possess seeds that are larger (increased size) than segregant seeds that lack the transgene which have normal levels of EMP4. The transgenic seeds also mature earlier than wild-type segregants.

Example 7.2

Maize Transformation with ZmMeg1-1::Emp4 Construct

The coding region of the maize EMP4 gene (SEQ ID No: 1) according to the invention is usefully expressed in an early stage of the BETL development.

EMP4 is fused to the ZmMeg1-1 promoter (Gutierrez-Marcos et al 2004) by performing an LR clonase reaction between the pEMP4-Entr (also named pBIOS1245) and pBIOS1027 (pBIOS1027 is a derivative of pBIOS342 containing the Meg1-1 promoter linked to an R1 R2 GATEWAY cassette). The resulting binary vector is then transferred to *agrobacterium* strain LB4404 (pSB1) and this strain is used to transform maize line A188. Analysis of the transformed plants indicates that some plants overexpress EMP4 and this increased expression is earlier than normal in seed development. These plants possess seeds that are larger (increased size) than segregant seeds that lack the transgene which have normal levels of EMP4. The transgenic seeds also mature earlier than wild-type segregants.

Example 7.3

Maize Transformation with pBETL1::EMP4 Construct

The coding region of the maize EMP4 gene (SEQ ID No: 1) according to the invention is usefully expressed in the BETL area.

EMP4 is fused to the BETL1 promoter (Hueros et al, 1999) by performing an LR clonase reaction between the plasmids pEMP4-Entr (also named pBIOS1245) and pBETL1 R1R2 bin (pBETL1 R1R2 bin is a derivative of pBIOS342 containing the BETL1 promoter linked to an R1 R2 GATEWAY cassette). The resulting binary vector is then transferred to *agrobacterium* strain LB4404 (pSB1) and this strain is used to transform maize line A188.

Analysis of the transformed plants indicates that some plants overexpress EMP4 and this expression is earlier than normal in seed development. These plants possess seeds that are larger (increased size) than segregant seeds that lack the transgene which have normal levels of EMP4. The transgenic seeds also mature earlier than wild-type segregants.

Example 7.4

Maize Transformation with pBETL2::EMP4 Construct

The coding region of the maize EMP4 gene (SEQ ID No: 1) according to the invention is usefully expressed in the BETL area.

EMP4 is fused to the BETL2 promoter (WO 99/50427) by performing an LR clonase reaction between the plasmids pEMP4-Entr (also named pBIOS1245) and pBETL2 R1R2 bin (pBETL2 R1R2 bin is a derivative of pBIOS342 containing the BETL2 promoter linked to an R1R2 GATEWAY cassette). The resulting binary vector is then transferred to *agrobacterium* strain LB4404 (pSB1) and this strain is used to transform maize line A188.

Analysis of the transformed plants indicates that some plants overexpress EMP4 and this expression is earlier than normal in seed development. These plants possess seeds that are larger (increased size) than segregant seeds that lack the transgene which have normal levels of EMP4. The transgenic seeds also mature earlier than wild-type segregants.

Example 7.5

Maize Transformation with pBETL9::EMP4 Construct

The coding region of the maize EMP4 gene (SEQ ID No: 1) according to the invention is usefully expressed in the BETL area. The BETL9 gene has an expression pattern similar to the BETL1 gene (Hueros et al, (1995)). However the promoter is more highly expressed than that of BETL1. The BETL9 promoter sequence (pBETL9) is represented by SEQ ID No: 32. The 1911 bp maize BETL9 promoter was PCRed from genomic DNA of the inbred line F2 using the primers: pBETL9forXho (SEQ ID No: 29) and pBETL9revXba (SEQ ID No: 30). These primers introduce an XhoI and an XbaI site 5' and 3' to the BETL9 promoter.

EMP4 was fused to the BETL9 promoter by performing an LR clonase reaction between the plasmids pEMP4-Entr (also named pBIOS1245) and pBIOS960 (pBIOS960 is a derivative of pBIOS342 containing the BETL9 promoter linked to an R1 R2 GATEWAY cassette and a CsVMV-GFP gene to mark seed containing the T-DNA). The resulting binary vector (pBIOS 1260 represented by FIG. 7) was then transferred to *Agrobacterium* strain LB4404 (pSB1) and this strain is used to transform maize line A188.

Analysis of the transformed plants indicates that some plants overexpress EMP4 and this expression is earlier than normal in seed development. These plants possess seeds that are larger (increased size) than segregant seeds that lack the transgene which have normal levels of EMP4. The transgenic GFP expressing seeds also mature earlier than wild-type segregants.

Example 8

Use of the Maize EMP4 Gene to Modify Plant Growth Rates

Constitutive overexpression of the maize EMP4 gene can be used to increase plant growth rate and/or to speed plant development whereas repression of EMP4 expression can reduce plant growth rates and/retard plant development. In some environmental conditions it is advantageous to have high growth rates and in others slower growth rates. Manipulation of EMP4 levels permits plants to be better adapted to the environment and to agronomic practices.

Example 8.1

Overexpression of the Maize EMP4 Gene

The maize EMP4 cDNA (SEQ ID No: 1) is cloned behind the constitutive promoter pCsVMV (Verdaguer et al, 1996) and cloned into a binary vector for agrobacterial mediated transformation of maize. This is achieved by an LR clonase reaction between pEMP4-Entr (also named pBIOS1245) and pBIOS886 (pBIOS886 is a derivative of pBIOS342 containing the CsVMV promoter linked to an R1 R2 GATEWAY cassette). The resulting binary vector is pBIOS 1259 represented in FIG. 8. Analysis of the transformed plants indicates that some plants have increased EMP4 levels. These plants have a faster rate of development and flower earlier than the control untransformed plants.

Example 8.2

Repression of the Maize EMP4 Gene Expression

Methods known in the art such as antisense, partial sense, RNAi can be used to reduce EMP4 expression. A 500 bp maize EMP4 region is selected that shows no significant homology to other genes. This region is cloned in an inverted orientation behind the constitutive CsVMV promoter and cloned into a binary vector for agrobacterial mediated transformation of maize. This is achieved by an LR clonase reaction between pEMP4-Entr (also named pBIOS1245) and pBIOS887 (pBIOS887 is a derivative of pBIOS342 containing the CsVMV promoter linked to an R2 R1 GATEWAY cassette followed by an intron and a R1 R2 GATEWAY cassette). Analysis of the transformed maize plants indicates that some plants have reduced EMP4 levels. These plants have a slower rate of development and flower later than the control untransformed plants.

Example 9

Regression of the Maize EMP4 Gene Expression in Internodes

A reduction in plant height is desirable to increase the harvest index and thus yield and also to prevent plant lodging. Ideally this reduction in height should be due to reduced growth of stem internodes and not effect growth of other vegetative organs such as leaves or roots so that photosynthesis and nutrient and water uptake is not compromised. Such promoters from sugarcane (c67 and c51) are described in WO 01/18211 and a homologue of gene c51 in maize also exhibits a stem-specific expression pattern. Thus the maize EMP4 antisense fragment is cloned behind the sugarcane c51 promoter that is preferentially expressed in stem internodes and cloned into a binary vector for agrobacterial mediated transformation of maize. Analysis of the maize transformed plants indicates that some plants have reduced EMP4 levels in internodes. These plants are dwarfed with internodes that are reduced in length. Plant seed yield is improved and lodging reduced.

REFERENCES

Allison et al. (1986), *Virology,* 154:9-20
An et al. (1986), *Plant Physiology,* 81:86-91.
Bechtold et al. (1993), <<*Comptes rendus Académie des Sciences Paris*>> Serie 3, 316:1194-1199.
Bevan et al. (1983), *Nature,* 304:184-187.
Chupeau, M C et al. (1989), *Biotechnology* vol. 7: pp. 503-508.
Consonni, G. et al. (2003), *Sex Plant Reprod* 15, 281-290.
Costa, L. M. et al. (2003), *Development.* October; 130(20): 5009-17.
Della-Cioppa et al. (1987), *Plant Physiology,* 84:965-968.
Depicker et al. (1992), *Mol. Gen. Genet.,* 235(2-3):389-396.
Elroy-Stein et al. (1989) *Proc Natl Acad Sci USA.* August;86(16):6126-30.
Finer J. et al. (1992) *Plant Cell Report* 11:323-328.
Franck et al. (1980), *Cell,* 21(1): 285-94.
Fromm M. et al. (1990), *Biotechnology,* 8:833-839.
Fu et al. (2002) *Plant Cell.* December; 14(12):3119-32.
Gallie, D. R. et al. (1989), *Molecular Biology of RNA,* pages 237-256.
Gomez et al. (2002), *Plant Cell,* 14, 599-610.
Gritz et al. (1883) *Gene.* November; 25(2-3):179-88.
Guerche et al. (1987), *Mol. Gen. Genet.,* 206:382
Gutierrez-Marcos J F, et al. (2004), *Plant Cell.* 16, 1288-301.
Hueros, G. et al. (1999b), *Plant Physiol.* 121, 1143-1152.
Ishida Y. et al. (1996), *Nature Biotechnol.* 14, 745-50.
Jenkins E. et al. (1999) *Plant Cell Environ* 22: 159-167.
Jobling, S. A., and Gehrke, L. (1987), *Nature,* 325:622-625.
Jouanin et al. (1987), *Plant Science,* 53:53-63.
Kay et al. (1987), *Science,* 236:1299-1302.
Komari T. et al. (1996), *Plant J.* 10:165-74.
Koncz et al. (1984), *EMBO J. May;* 3(5):1029-37.
Lander E. S. et al. (1987), *Genomics* 1, 174-181.
Lommel, S. A. et al. (1991), *Virology,* 81:382-385.
Lurin et al. (2004), *Plant Cell.* August;16(8):2089-103.
Maas et al. (1991), *Plant Molecular Biology,* 16:199.
Macejack, D. G., and P. Sarnow (1991), *Nature,* 353:90-94.
Maitz, M. et al. (2000) *Plant J.* 23, 29-42.
McElroy et al. (1990), *Plant Cell,* 2:163-171.
McElroy et al. (1991) *Mol Gen Genet.* 231, 150-60.
Morris et al. (1992), *Virology,* 187:633
Mullis, K B (1987), *Methods in Enzymology* 155:335.
Neuffer, M. G., and Sheridan, F. (1980), *Genetics* 95, 929-944.
Neuhaus et al. (1987), *Theoretical and applied Genet.,* 75(1): 30-36
Ohta et al. (1990), *Plant Cell Physiology,* 31:805.
Opsahl-Ferstad, et al. (1997), *Plant J.* 12, 235-246.
O'Sullivan, D. M. et al. (2001) *TAG* 103, 425-432.
Sambrook et al. (1989), *Molecular Cloning, A Laboratory Manual,* Cold Spring Harbour Laboratory Press p. 9.54-9.62.
Scanlon, M. J. et al. (1994) *Genetics* 136, 281-294.
Scanlon, M. J. et al. (1997) *Plant J.* 12, 901-909.
Schocher et al. (1986). *Biotechnology* 4:1093-1096.
Sheridan, W. F., and Neuffer M. G. (1980) *Genetics* 95, 945-960.
Snowdon et al. (1996), *Plant Molecular Biology,* 31:689.
Vancanneyt et al. (1990) *Mol. Gen. Genet.* January;220(2): 245-50.
Verdaguer B. et al. (1996) *Plant Mol. Biol.* 31, 1129-39.
Watson et al. (1994) *Ed. De Boeck Université,* pp 273-292.
White, J. et al. (1990) *Nucl. Acid. Res.* 18, 1062.
Wright, A. D. et al. (1992) *Plant Cell* 4, 711-719.
Yoder et al., (1993) *Biotechnology,* 12, 263-292.

---

The invention claimed is:

1. A transgenic plant or part thereof, comprising, as a transgene, an isolated nucleic acid molecule encoding a protein which alters plant or endosperm development wherein the nucleic acid molecule comprises a nucleotide sequence selected from the group consisting of:
   a) a nucleotide sequence encoding a protein having the amino acid sequence of SEQ ID NO:2 or an amino acid sequence that is at least 90% identical to SEQ ID NO:2, and
   b) a nucleotide sequence of SEO ID NO:1 or a nucleotide sequence that is at least 90% identical to SEQ ID NO:1;
   wherein said nucleic acid molecule is operably linked to a promoter allowing expression of said nucleic acid molecule in the endosperm, wherein said transgenic plant has increased growth rate when compared to control plants that lack the transgene or said transgenic plant exhibits larger seeds that mature early when compared to control plants that lack the transgene.

2. The plant or part thereof according to claim 1, wherein said plant or part thereof is a cereal or a plant that is capable of producing oil.

3. The plant or part thereof according to claim 1, wherein said plant or part thereof is selected from the group consisting of maize, rice, sorghum, wheat, barley, rye, rape, pea, *brassica napus*, sunflower and sugar cane.

4. A method for obtaining a plant having increased seed size comprising:
   a) transforming at least a plant cell or plant tissue with an expression vector comprising an expression cassette comprising a promoter which allows expression in the endosperm operably linked to a nucleic acid molecule encoding a protein which alters plant or endosperm development comprising a nucleic acid sequence selected from the group consisting of:
   i. a nucleotide sequence encoding a protein having the amino acid sequence of SEQ ID NO:2 or an amino acid sequence that is at least 90% identical to SEQ ID NO:2; and
   ii. a nucleotide sequence of SEQ ID NO:1 or a nucleotide sequence that is at least 90% identical to SEQ ID NO:1;
   b) cultivating the transformed cell(s) or plant tissue so as to generate a plant containing in its genome at least said expression cassette whereby said plant has increased seed size, as compared to a non-transformed plant.

5. A method for increasing plant growth rate comprising;
   a) transforming at least a plant cell or plant tissue with an expression vector comprising an expression cassette comprising a promoter which allows expression in the endosperm, operably linked to a nucleic acid molecule encoding a protein which alters plant or endosperm development comprising a sequence selected from the group consisting of:
   i. a nucleotide sequence encoding a protein having the amino acid sequence of SEQ ID NO:2 or an amino acid sequence that is at least 90% identical to SEQ ID NO:2 and
   ii. a nucleotide sequence of SEQ ID NO:1 or a nucleotide sequence that is at least 90% identical to SEQ ID NO1;
   b) cultivating the transformed cell(s) or plant tissue so as to generate a plant containing in its genome at least said expression cassette wherein said plant has increased growth rate, as compared to a non-transformed plant.

6. The plant of claim 1, wherein said promoter is a BETL-specific promoter.

7. The plant of claim 1, which further comprises a selection marker gene for plants.

* * * * *

SEQUENCE LISTING

```
<160> NUMBER OF SEQ ID NOS: 35

<210> SEQ ID NO 1
<211> LENGTH: 1963
<212> TYPE: DNA
<213> ORGANISM: Zea mays

<400> SEQUENCE: 1
atcgcccgca tgtgcatctc agtccgccac gggccacagc cggcctcact ccgcaagtcc      60
gcgaccatgc ggtgcaccct ctccgcccct ctccggcgct gtctctcctc caccggcgcc     120
gccgatccta gcctagtctc ttcagctgag catgcgtacc ggctcctccg ccgccaccac     180
tccgacccgc agaggctctc tgccgcgctg tccgcgtcgg gtctcgacgc ctcctcgccg     240
cacctcctcg acgccgtcct ccgccgctgt ggcgctgcct cctccctcgc gctgcacttc     300
ttccactggt gctccccgtc gctgccctcg ccgctcccgt cctccctagc gctcctcgcc     360
aagtccttct cccgcgcctc ctccgcgccg tcccgtccc tactcgcgcc gctcccctct      420
caactccttg gcccctccct cctctgcccc gtcctgcgcc gcctcccgca accgcgcctc     480
ctgccgttcg cgctctcact actctccgcc cgccccgacc acgaccagcc cgccctcttt     540 cttccctcc tcgagtccct ctccaaggcc ggccacgtcc tcaccgccga gcagcttgtc      600
gaggagctcc agcccggct cccgctttcg ctccgccact atacggcctt gctctacgga      660
tggtgccgtc agggcaagct cgacgaggcc aagcacgtgc tcgctcgcat gaaggctgcg     720
gatgttgccc ttgacgtcgt cgtatttaac accctgctcg ctggcttcgt cgcggaaggg     780
```

```
agattcgagg acgcgttcga gctggcgggg cagatggagc agcgtggctg tccaccgaac    840
gcggtgtcgt acaccaccct gattcagggg cttggcgcga gggggagagt tgatgaggcc    900
atgcgcatgt ttgtggaaat gcgaaggaag gggtgcgcgc ccgatgctgt cacgtacggc    960
accctggtta acacgttttg caaggctggc aagatatccc aggggtacga gttcttggat   1020
gctatgtcga gggatggcct gcgggtggac gctgccgtgt accatggttt ctttgtagca   1080
cacgagaaga aggagcagct tgaggagtgc ttggagctga tggagaggat gcgggagtgc   1140
cggtgtccac cagatctcaa gatatacaat gtggtgattc ggttggcctg caggcttggg   1200
gagaccaagc aagccatgac attgtggaat gagatggaaa gtgctgggct cagtcctgtg   1260
gtcgatacat ttgctatcgt ggtgagtggc cttgttgggc agggtttgct gattgaggca   1320
tgtagttatt ttaaagacat ggttgggagg gggctctttg tggtaccgca atatggggtg   1380
ctgaaggacc tcctcaatgc gttggtcaga gatgagaaac ttgagcttgc aaaggatgtt   1440
tggaaatgta ttgtgagcaa aggctgtgag ctcaatgtga gtgcatggac tatctggatt   1500
catgcactgt ttgcgaagaa acatgtcaag gaggcctgcc tgtattgctt agacatgcta   1560
gaggcaggac tgatgccaca gcctgacaca tttgcaaagt tgatgaaggg gctgaagaag   1620
ttgtacaacc gtcagattgc tgctgagatt actgagaagg ttaggaagat ggcggaggag   1680
agacatgtta gctttaagat gtataagaga cgtggggtga gggatcttga agagaaactc   1740
aaggcaaaga ggagaggaca gaaaaagagg catctgcggc agcctggtca tggtcagtct   1800
agtagggatg ctgcaatttt ggatgcttct gatgaagtag aattttccgg ctaattgaaa   1860
tagaattcat tgggggcaat gcatctctgt tcatttgaat tgttttgggg agtgatagac   1920
ttactaaaca ataaaggagt gctggtgatc aaaaaaaaaa aaa                     1963
```

<210> SEQ ID NO 2
<211> LENGTH: 614
<212> TYPE: PRT
<213> ORGANISM: Zea mays

<400> SEQUENCE: 2

```
Met Cys Ile Ser Val Arg His Gly Pro Gln Pro Ala Ser Leu Arg Lys
1               5                   10                  15

Ser Ala Thr Met Arg Cys Thr Leu Ser Ala Pro Leu Arg Arg Cys Leu
            20                  25                  30

Ser Ser Thr Gly Ala Ala Asp Pro Ser Leu Val Ser Ser Ala Glu His
        35                  40                  45

Ala Tyr Arg Leu Leu Arg Arg His His Ser Asp Pro Gln Arg Leu Ser
    50                  55                  60

Ala Ala Leu Ser Ala Ser Gly Leu Asp Ala Ser Ser Pro His Leu Leu
65                  70                  75                  80

Asp Ala Val Leu Arg Arg Cys Gly Ala Ala Ser Ser Leu Ala Leu His
                85                  90                  95

Phe Phe His Trp Cys Ser Pro Ser Leu Pro Ser Pro Leu Pro Ser Ser
                100                 105                 110

Leu Ala Leu Leu Ala Lys Ser Phe Ser Arg Ala Ser Ser Ala Pro Ser
            115                 120                 125

Pro Ser Leu Leu Ala Pro Leu Pro Ser Gln Leu Leu Gly Pro Ser Leu
        130                 135                 140

Leu Cys Pro Val Leu Arg Arg Leu Pro Gln Pro Arg Leu Leu Pro Phe
145                 150                 155                 160

Ala Leu Ser Leu Leu Ser Ala Arg Pro Asp His Asp Gln Pro Ala Leu
```

-continued

```
                165                 170                 175
Phe Leu Ser Leu Leu Glu Ser Leu Ser Lys Ala Gly His Val Leu Thr
            180                 185                 190
Ala Glu Gln Leu Val Glu Glu Leu Gln Pro Arg Leu Pro Leu Ser Leu
        195                 200                 205
Arg His Tyr Thr Ala Leu Leu Tyr Gly Trp Cys Arg Gln Gly Lys Leu
    210                 215                 220
Asp Glu Ala Lys His Val Leu Ala Arg Met Lys Ala Asp Val Ala
225                 230                 235                 240
Leu Asp Val Val Val Phe Asn Thr Leu Leu Ala Gly Phe Val Ala Glu
                245                 250                 255
Gly Arg Phe Glu Asp Ala Phe Glu Leu Ala Gly Gln Met Glu Gln Arg
            260                 265                 270
Gly Cys Pro Pro Asn Ala Val Ser Tyr Thr Thr Leu Ile Gln Gly Leu
        275                 280                 285
Gly Ala Arg Gly Arg Val Asp Glu Ala Met Arg Met Phe Val Glu Met
    290                 295                 300
Arg Arg Lys Gly Cys Ala Pro Asp Ala Val Thr Tyr Gly Thr Leu Val
305                 310                 315                 320
Asn Thr Phe Cys Lys Ala Gly Lys Ile Ser Gln Gly Tyr Glu Phe Leu
                325                 330                 335
Asp Ala Met Ser Arg Asp Gly Leu Arg Val Asp Ala Ala Val Tyr His
            340                 345                 350
Gly Phe Phe Val Ala His Glu Lys Lys Glu Gln Leu Glu Glu Cys Leu
        355                 360                 365
Glu Leu Met Glu Arg Met Arg Glu Cys Arg Cys Pro Pro Asp Leu Lys
    370                 375                 380
Ile Tyr Asn Val Val Ile Arg Leu Ala Cys Arg Leu Gly Glu Thr Lys
385                 390                 395                 400
Gln Ala Met Thr Leu Trp Asn Glu Met Glu Ser Ala Gly Leu Ser Pro
                405                 410                 415
Val Val Asp Thr Phe Ala Ile Val Val Ser Gly Leu Val Gly Gln Gly
            420                 425                 430
Leu Leu Ile Glu Ala Cys Ser Tyr Phe Lys Asp Met Val Gly Arg Gly
        435                 440                 445
Leu Phe Val Val Pro Gln Tyr Gly Val Leu Lys Asp Leu Leu Asn Ala
    450                 455                 460
Leu Val Arg Asp Glu Lys Leu Glu Leu Ala Lys Asp Val Trp Lys Cys
465                 470                 475                 480
Ile Val Ser Lys Gly Cys Glu Leu Asn Val Ser Ala Trp Thr Ile Trp
                485                 490                 495
Ile His Ala Leu Phe Ala Lys Lys His Val Lys Glu Ala Cys Leu Tyr
            500                 505                 510
Cys Leu Asp Met Leu Glu Ala Gly Leu Met Pro Gln Pro Asp Thr Phe
        515                 520                 525
Ala Lys Leu Met Lys Gly Leu Lys Lys Leu Tyr Asn Arg Gln Ile Ala
    530                 535                 540
Ala Glu Ile Thr Glu Lys Val Arg Lys Met Ala Glu Glu Arg His Val
545                 550                 555                 560
Ser Phe Lys Met Tyr Lys Arg Arg Gly Val Arg Asp Leu Glu Glu Lys
                565                 570                 575
Leu Lys Ala Lys Arg Arg Gly Gln Lys Lys Arg His Leu Arg Gln Pro
            580                 585                 590
```

Gly His Gly Gln Ser Ser Arg Asp Ala Gly Asn Leu Asp Ala Ser Asp
       595                 600                 605

Glu Val Glu Phe Ser Gly
    610

<210> SEQ ID NO 3
<211> LENGTH: 5282
<212> TYPE: DNA
<213> ORGANISM: Zea mays

<400> SEQUENCE: 3

| | | | | | |
|---|---|---|---|---|---|
| atgcaatatc | cgaatgattc | taggggcgg | gcagtactca | tggatacaac | ccttcatcaa | 60 |
| ctccatggtg | ttcttcatct | tgctggaatc | ctccttcttg | atcagccatt | cccacttctg | 120 |
| catgaaagaa | atcgcatcat | acatgatcat | agtagcattg | cttggaaact | tttttcgatt | 180 |
| gacatcttgt | tcagttacgc | cataaggccc | agactatgct | tgcaaacaga | aaagatgaa | 240 |
| gggattgagg | gatatgtgac | ttcatcacat | catcgataga | gaaatatct | tctaccaatc | 300 |
| taggagtccg | tctccagttc | aaaataatgt | gaatacagtt | ccaaacataa | ttcgccaacg | 360 |
| ggcaaaagaa | aaaaaatgtg | gtcaatagtc | tccggttccc | agcaaagggc | acatgcacca | 420 |
| ctacttttcc | aatccttttt | ttaattcatg | gtcgcttgc | attttctgt | tgtaaagtag | 480 |
| ccacaagaac | accctgatct | taagaggaac | tttgcatttc | cagatgatgt | tataaatatt | 540 |
| attcctgacc | ccccatcaaa | cataaacctg | tacaacgacc | tagtagagaa | catattagag | 600 |
| ttctctaagg | tccagatcac | tgtatctctc | ccatgtgaaa | tcccatgatc | ctgcatttca | 660 |
| gatttaagaa | tcttccgttc | gctgaaatcc | ttattagaaa | gtggtctctc | aaattccaac | 720 |
| caaccattat | ctccatcgaa | gcaatcaact | acaaggacat | cttcatcctt | gcaaatttca | 780 |
| tatagatttg | gatatttgat | acttagaggt | acctctccca | tccaagtatc | cttccaaaac | 840 |
| agagtgcctt | ctccgtttcg | gacaatgttc | actaccccca | ttggaacaaa | tgtttaactt | 900 |
| tgggaaattt | ggatccatac | cattaaaaga | tcaccacttt | ggatccatac | cattactatc | 960 |
| tcacttacat | gtgggtccac | atgagtcaat | gacatgtggg | gtccatggta | tatatctaaa | 1020 |
| gtttggatct | tttaatggta | tagatccaat | tgttccttaa | ctttatgtaa | tccttgccaa | 1080 |
| atctgagaag | ccccccttgg | ttttagattt | aaagaagttg | atccctgtca | tatacttagc | 1140 |
| tttaatgatt | ttgtaccaca | tatcctccta | tccctaaaca | atcctttaaa | tccatttaac | 1200 |
| caataagcat | tcattcatta | gcctagtatt | tatgatacca | agaccctctt | gtctttaggt | 1260 |
| ctagtaacca | tgtcccatt | cgccatgtga | gaattggagt | ttgtggttgt | ataatatgtt | 1320 |
| tgttgtatat | tattttcgtg | aacatatgtc | gtgtggatca | attaatattt | aatgtgcaat | 1380 |
| gtgaattgag | caaattacaa | ataaattttg | ttaaaaaatt | tcttttcctg | taaaaaaaca | 1440 |
| gtaaaacagt | acattttctt | ggaaaaccat | cgatttagga | tgatttaccg | ctggtttttc | 1500 |
| atctataaaa | cctaccaaat | ttagggcctg | tttggtttgt | gactaaatgt | gccacacttt | 1560 |
| gcctaagttt | agtcgttcga | attgaataac | tacctttaga | cagaaaagtt | agataaaata | 1620 |
| tgacaacgag | gtagtgaacc | aaataggccc | ttagttttgt | ttagactgga | caaatcggtt | 1680 |
| aggcggattt | ttaggggcaa | acggtctgct | gtcaatacaa | cagttttcgt | tgggtgcatt | 1740 |
| tcgctttcgc | atcgcccgca | tgtgcatctc | agtccgccac | gggccacagc | cggcctcact | 1800 |
| ccgcaagtcc | gcgaccatgc | ggtgcaccct | ctccgcccct | ctccggcgct | gtctctcctc | 1860 |
| caccggcgcc | gccgatccta | gcctagtctc | ttcagctgag | catgcgtacc | ggctcctccg | 1920 |
| ccgccaccac | tccgacccgc | agaggctctc | tgccgcgctg | tccgcgtcgg | gtctcgacgc | 1980 |

```
ctcctcgccg cacctcctcg acgccgtcct ccgccgctgt ggcgctgcct cctccctcgc    2040
gctgcacttc ttccactggt gctccccgtc gctgccctcg ccgctcccgt cctccctagc    2100
gctcctcgcc aagtccttct cccgcgcctc ctccgcgccg tccccgtccc tactcgcgcc    2160
gctcccctct caactccttg gcccctccct cctctgcccc gtcctgcgcc gcctcccgca    2220
accgcgcctc ctgccgttcg cgctctcact actctccgcc cgccccgacc acgaccagcc    2280
cgccctcttt ctttccctcc tcgagtccct ctccaaggcc ggcacgtcc tcaccgccga     2340
gcagcttgtc gaggagctcc agccccggct cccgctttcg ctccgccact atacggcctt    2400
gctctacgga tggtgccgtc agggcaagct cgacgaggcc aagcacgtgc tcgctcgcat    2460
gaaggctgcg gatgttgccc ttgacgtcgt cgtatttaac accctgctcg ctggcttcgt    2520
cgcggaaggg agattcgagg acgcgttcga gctggcgggg cagatggagc agcgtggctg    2580
tccaccgaac gcggtgtcgt acaccaccct gattcagggg cttggcgcga ggggagagt    2640
tgatgaggcc atgcgcatgt tgtggaaat gcgaaggaag gggtgcgcgc ccgatgctgt    2700
cacgtacggc accctggtta acacgttttg caaggctggc aagatatccc aggggtacga    2760
gttcttggat gctatgtcga gggatggcct gcgggtggac gctgccgtgt accatggttt    2820
ctttgtagca cacgagaaga aggagcagct tgaggagtgc ttggagctga tggagaggat    2880
gcgggagtgc cggtgtccac cagatctcaa gatatacaat gtggtgattc ggttggcctg    2940
caggcttggg gagaccaagc aagccatgac attgtggaat gagatggaaa gtgctgggct    3000
cagtcctgtg gtcgatacat tgctatcgt ggtgagtggc cttgttgggc agggtttgct     3060
gattgaggca tgtagttatt ttaaagacat ggttgggagg gggctctttg tggtaccgca    3120
atatggggtg ctgaaggacc tcctcaatgc gttggtcaga gatgagaaac ttgagcttgc    3180
aaaggatgtt tggaaatgta ttgtgagcaa aggctgtgag ctcaatgtga gtgcatggac    3240
tatctggatt catgcactgt ttgcgaagaa acatgtcaag gaggcctgcc tgtattgctt    3300
agacatgcta gaggcaggac tgatgccaca gcctgacaca tttgcaaagt tgatgaaggg    3360
gctgaagaag ttgtacaacc gtcagattgc tgctgagatt actgagaagg ttaggaagat    3420
ggcggaggag agacatgtta gctttaagat gtataagaga cgtggggtga gggatcttga    3480
agagaaactc aaggcaaaga ggagaggaca gaaaaagagg catctgcggc agcctggtca    3540
tggtcagtct agtagggatg ctggcaattt ggatgcttct gatgaagtag aattttccgg    3600
ctaattgaaa tagaattcat tggggcaat gcatctctgt tcatttgaat tgtttggg      3660
agtgatagac ttactaaaca ataaaggagt gctggtgatc atgccttgcc atcataatat   3720
tattcttatg ctaaagatgt attgggtttc aggcaagagc caagtggtac atcgattaca    3780
tgtgaagttg tgtgccaaga gttactgacc atgaggaggt aactattttc atcctaccta    3840
cactgtgcaa attagaactt cattcaggtg tttattgctg tttttgtagg tagaagatat    3900
gacgggtgat ttatttgatc tgcacttagg ccttgtttgg ctgtacctca atccactcca    3960
atccacgtgt attggggtgg attaagggc cgttcggtta ctgcagaatg aagtcctgga     4020
acaattccta tccgaattgt ttctctcatt tatataaatt ttgattagct ggaataattc    4080
ctggtgtatt cctatgcaaa cagggcctaa gggtttgtct agctacactg caatccatct    4140
caatccacat gtggattggg gtgaattgca acgtaaccaa ataagggcca aggtggaagc    4200
aatgtttcag attattatct tttttactc ctgaaagcag tgggttttga aacccgtttt     4260
tttcttcgaa atgagggaaa cagagataat catgtatacg taagtttggt gctggtgcaa    4320
ccagttgggc caaaatttgt agctgatgaa gcttcgttgt tacttttctt tgacttgctt    4380
```

-continued

| | |
|---|---|
| atctcttcac tcttccatcc gtccaagaat ttttacgagc caatcacagg tgcacaccac | 4440 |
| tattggtgaa tacaccaaaa agagggataa aagaggagag ggagggatta aatgagtgac | 4500 |
| caagtgtcca cttgacccct ttttataggg gctctgtttg ttttctttta agattatata | 4560 |
| atcgagctca tagattatat aagcacctga tattctactt atggattaca taatctaggt | 4620 |
| atctagatta cataatctat ttaataatct gtgttgtttg tttgtctctt aacttattta | 4680 |
| agctggatta tataatttag aggataaaca aacgggacca tagaagggaa ttttgtagct | 4740 |
| gatgaagctt cattgttact tcgcgctttt acttgcttat cccttcactc tttcttccgc | 4800 |
| ccatccaaga atctgtatga gccaatcaca ggtgcgcacc aatgttggtg agtacgagaa | 4860 |
| aatttatat ttgggacttc aaacaaaaag attcatagtt ttgccatctg aatcgttcgc | 4920 |
| tttgcaaaaa caagattcat aacatcttcc aattgatttc aatatcattt catgtatttt | 4980 |
| cttctttttc ctatttttc aagtatttgg agaccttgcc cttaagtatt tctacgttcc | 5040 |
| aatggagctc gactgtcgcc tgctcccgtg ctcgccccgg ccgccgccgc cgcatgcgat | 5100 |
| cccgcgctgg caatgtcagc cgccaatcct tgtgaatttt tggtcgtttg ctccaatctt | 5160 |
| gtggattctg gtcgctggtt ccaatcctaa acttgcaaag gtccacatac cctgccctg | 5220 |
| ctatgtagga gtctgctacg gcgcatgagc gcggtctgaa gtgacggctt cggccttatc | 5280 |
| cg | 5282 |

<210> SEQ ID NO 4
<211> LENGTH: 1890
<212> TYPE: DNA
<213> ORGANISM: Oryza sativa

<400> SEQUENCE: 4

| | |
|---|---|
| atgaaccaaa aagaaaagaa aaatgaaccg ggcaagcatt ctgggcttgc gcagttgcgc | 60 |
| cacactgcca cagtccagcc caccatgcgg cgcctcctct ccgctccgct gcgccgccgc | 120 |
| ctatgcacgg cggccgtggc cgcggcggcg cccgacccgg ccctcgcctc ctccgcggag | 180 |
| ctcgcgtacc gcctcctccg ccgccaccac tccgacccca agaggctcac cgccgcgctc | 240 |
| tccggctcgg gcctcgaccc gacctcgccg cgcctcctcg acgccgtcct ccgccgctgc | 300 |
| ggcgccgcct ccgcgctcgc gctccacttc ttccactggt gctccccgtc gctgccgccg | 360 |
| ccggggccgc tcccttcctc cctcgcgctc ctcgccaagt ccttctcccg cgcctcctcc | 420 |
| gcgccgtccc cttccctcct cgcgccgctc cccgcccagc tcctctcccc gtccctcctc | 480 |
| tccccgtcc tccgccgcct cccgccccg cgcctcctcc ccttcgcgct ctcactcctc | 540 |
| tccgcgcgcc caaccacga ccaccctcg ctcttcctct ccctcctcga gtccctcgcc | 600 |
| aagaccggcc atgtcgccgt cgccgagcag ctcgtcgagg agctccagcc caggctcccg | 660 |
| ctctcgctcc gccactacac cgcgctgctc tacgggtggt gccgcatggg caagctcgac | 720 |
| gaggccaagc acgtgctcgc ccgcatgaag gccgcggagg tcgccccgga cgtcgtcgtc | 780 |
| ttcaacaccc tcctcgccgg cttcgtcgcc gacgggcggt tcgaggacgc gttcgagctg | 840 |
| gcccgggaga tggagcggcg tggctgcccg ccgaacgccg tgtcgtacac caccctgatg | 900 |
| caggggcttg gcgccagggg gagggttgat gaggcaatgc gggtgtttgt ggaaatgcgc | 960 |
| aggaaggggt gtgcaccgga ttccgtcacc tatggcactc tggttactgc gttctgcaag | 1020 |
| gctggtagga tatcacaggg atatgagttc ttggacgtca tggcaaggga gggtctgcgg | 1080 |
| gtggacgccg gcgtgtacct cgggttcttc gtcgcgcacg agaagaagga gcagcttgag | 1140 |
| gagtgcttgg agttgatgga gaggatgagg gagtgcaggt gcccgccaga cctcagcatc | 1200 |

```
tacaatgtgg tgatcaggtt ggcctgcaaa ctcggggaga cgaagcaggc tgtggcattg    1260
tggaacgaga tggagaccaa cgagcttagt cccggggttg acacatttgc tatcatggtg    1320
actggcctcg ttggccaagg cgtgctggtt gaggcctgcg gttatttcaa ggacatggtt    1380
gggaggggac tctttgttgc accccagtat ggggtgctga aggacctcct caattcattg    1440
gtcagagatc agaaacttga gcttgcaaag gatgtttggg gatgcattat gaccaaaggc    1500
tgtgagctca attttggcgc atggacaatc tggattcatg cactgtacgc aaagaaacac    1560
gtcaaggagg cctgcatgta ttgcttggac atgcttgacg ctggtctgat gccgcagccc    1620
gacacatttg caaagctgat gaagggactg aagaagctct acaacaggca gattgctgct    1680
gagatcactg agaaggtgag gaagatggcg gaggagagac atgttagctt caagatgtat    1740
aagaggcgtg gggtgaggga tcttgaagag aagcctaagg caaagagaaa gaaagggcag    1800
aaaaggagtc gcttgaggca ggctggtcag aatcaatcca ataggcatgc tgacaaaact    1860 gaccttttg atgattttga tgatgaataa                                     1890
```

<210> SEQ ID NO 5
<211> LENGTH: 629
<212> TYPE: PRT
<213> ORGANISM: Oryza sativa

<400> SEQUENCE: 5

```
Met Asn Gln Lys Glu Lys Lys Asn Glu Pro Gly Lys His Ser Gly Leu
1               5                   10                  15

Ala Gln Leu Arg His Thr Ala Thr Val Gln Pro Thr Met Arg Arg Leu
            20                  25                  30

Leu Ser Ala Pro Leu Arg Arg Arg Leu Cys Thr Ala Ala Val Ala Ala
        35                  40                  45

Ala Ala Pro Asp Pro Ala Leu Ala Ser Ser Ala Glu Leu Ala Tyr Arg
    50                  55                  60

Leu Leu Arg Arg His His Ser Asp Pro Lys Arg Leu Thr Ala Ala Leu
65                  70                  75                  80

Ser Gly Ser Gly Leu Asp Pro Thr Ser Pro Arg Leu Leu Asp Ala Val
                85                  90                  95

Leu Arg Arg Cys Gly Ala Ala Ser Ala Leu Ala Leu His Phe Phe His
            100                 105                 110

Trp Cys Ser Pro Ser Leu Pro Pro Gly Pro Leu Pro Ser Ser Leu
            115                 120                 125

Ala Leu Leu Ala Lys Ser Phe Ser Arg Ala Ser Ser Ala Pro Ser Pro
    130                 135                 140

Ser Leu Leu Ala Pro Leu Pro Ala Gln Leu Leu Ser Pro Ser Leu Leu
145                 150                 155                 160

Ser Pro Val Leu Arg Arg Leu Pro Pro Arg Leu Leu Pro Phe Ala
                165                 170                 175

Leu Ser Leu Leu Ser Ala Arg Pro Asn His Asp His Pro Ser Leu Phe
            180                 185                 190

Leu Ser Leu Leu Glu Ser Leu Ala Lys Thr Gly His Val Ala Val Ala
        195                 200                 205

Glu Gln Leu Val Glu Glu Leu Gln Pro Arg Leu Pro Leu Ser Leu Arg
    210                 215                 220

His Tyr Thr Ala Leu Leu Tyr Gly Trp Cys Arg Met Gly Lys Leu Asp
225                 230                 235                 240

Glu Ala Lys His Val Leu Ala Arg Met Lys Ala Glu Val Ala Pro
                245                 250                 255
```

Asp Val Val Val Phe Asn Thr Leu Leu Ala Gly Phe Val Asp Gly
          260                 265                 270

Arg Phe Glu Asp Ala Phe Glu Leu Ala Arg Glu Met Glu Arg Gly
              275                 280                 285

Cys Pro Pro Asn Ala Val Ser Tyr Thr Thr Leu Met Gln Gly Leu Gly
290                 295                 300

Ala Arg Gly Arg Val Asp Glu Ala Met Arg Val Phe Val Glu Met Arg
305                 310                 315                 320

Arg Lys Gly Cys Ala Pro Asp Ser Val Thr Tyr Gly Thr Leu Val Thr
              325                 330                 335

Ala Phe Cys Lys Ala Gly Arg Ile Ser Gln Gly Tyr Glu Phe Leu Asp
          340                 345                 350

Val Met Ala Arg Glu Gly Leu Arg Val Asp Ala Gly Val Tyr Leu Gly
          355                 360                 365

Phe Phe Val Ala His Glu Lys Lys Glu Gln Leu Glu Glu Cys Leu Glu
370                 375                 380

Leu Met Glu Arg Met Arg Glu Cys Arg Cys Pro Pro Asp Leu Ser Ile
385                 390                 395                 400

Tyr Asn Val Val Ile Arg Leu Ala Cys Lys Leu Gly Glu Thr Lys Gln
                  405                 410                 415

Ala Val Ala Leu Trp Asn Glu Met Glu Thr Asn Glu Leu Ser Pro Gly
              420                 425                 430

Val Asp Thr Phe Ala Ile Met Val Thr Gly Leu Val Gly Gln Gly Val
          435                 440                 445

Leu Val Glu Ala Cys Gly Tyr Phe Lys Asp Met Val Gly Arg Gly Leu
450                 455                 460

Phe Val Ala Pro Gln Tyr Gly Val Leu Lys Asp Leu Leu Asn Ser Leu
465                 470                 475                 480

Val Arg Asp Gln Lys Leu Glu Leu Ala Lys Asp Val Trp Gly Cys Ile
                  485                 490                 495

Met Thr Lys Gly Cys Glu Leu Asn Phe Gly Ala Trp Thr Ile Trp Ile
              500                 505                 510

His Ala Leu Tyr Ala Lys Lys His Val Lys Glu Ala Cys Met Tyr Cys
          515                 520                 525

Leu Asp Met Leu Asp Ala Gly Leu Met Pro Gln Pro Asp Thr Phe Ala
530                 535                 540

Lys Leu Met Lys Gly Leu Lys Lys Leu Tyr Asn Arg Gln Ile Ala Ala
545                 550                 555                 560

Glu Ile Thr Glu Lys Val Arg Lys Met Ala Glu Arg His Val Ser
                  565                 570                 575

Phe Lys Met Tyr Lys Arg Arg Gly Val Arg Asp Leu Glu Glu Lys Pro
          580                 585                 590

Lys Ala Lys Arg Lys Lys Gly Gln Lys Arg Ser Arg Leu Arg Gln Ala
              595                 600                 605

Gly Gln Asn Gln Ser Asn Arg His Ala Asp Lys Thr Asp Leu Phe Asp
          610                 615                 620

Asp Phe Asp Asp Glu
625

<210> SEQ ID NO 6
<211> LENGTH: 2520
<212> TYPE: DNA
<213> ORGANISM: Oryza sativa

<400> SEQUENCE: 6

-continued

| | |
|---|---|
| ttattttta ttagtagaaa gtagagtgaa gatctgatag aaaataataa gtagcccata | 60 |
| atattatagc agaaaaacaa tgtttattac gacttactca gttactctgt tgtgcattag | 120 |
| agctgtggtt agctcaaacc ggtgctgcct atcatctata tgcgttaaat gatgcatgga | 180 |
| tatgaattcg gtttgttaca gctgaccctg ttgattctgc acagcagatc gcagtatcag | 240 |
| actgaaattg tgagtgcaat ctagccataa accaacatgt cactttcgaa atgacaccgt | 300 |
| atgatcatac tctgatacgt ggagagtact ccctccgtcc tataaaaaat gaatcttccc | 360 |
| ataaaaaatg aatctgattt atagtaatag aatatattaa atctggtact aagttgttcc | 420 |
| tataatcatg ttgccacgaa aaagaaaaat aaaaaatgaa ccaaaaagaa aagaaaaatg | 480 |
| aaccgggcaa gcattctggg cttgcgcagt tgcgccacac tgccacagtc cagcccacca | 540 |
| tgcggcgcct cctctccgct ccgctgcgcc gccgcctatg cacggcggcc gtggccgcgg | 600 |
| cggcgcccga cccggccctc gcctcctccg cggagctcgc gtaccgcctc ctccgccgcc | 660 |
| accactccga ccccaagagg ctcaccgccg cgctctccgg ctcgggcctc gacccgacct | 720 |
| cgccgcgcct cctcgacgcc gtcctccgcc gctgcggcgc cgcctccgcg ctcgcgctcc | 780 |
| acttcttcca ctggtgctcc ccgtcgctgc cgccgccggg gccgctccct tcctccctcg | 840 |
| cgctcctcgc caagtccttc tcccgcgcct cctccgcgcc gtcccttcc ctcctcgcgc | 900 |
| cgctccccgc ccagctcctc tccccgtccc tcctctcccc cgtcctccgc cgcctcccgc | 960 |
| ccccgcgcct cctcccttc gcgctctcac tcctctccgc gcgcccaac cacgaccacc | 1020 |
| cctgctctct cctctccctc ctcgagtccc tcgccaagac cggccatgtc gccgtcgccg | 1080 |
| agcagctcgt cgaggagctc cagcccaggc tcccgctctc gctccgccac tacaccgcgc | 1140 |
| tgctctacgg gtggtgccgc atgggcaagc tcgacgaggc caagcacgtg ctcgcccgca | 1200 |
| tgaaggccgc ggaggtcgcc ccggacgtcg tcgtcttcaa caccctcctc gccggcttcg | 1260 |
| tcgccgacgg gcggttcgag gacgcgttcg agctggcccg ggagatggag cggcgtggct | 1320 |
| gcccgccgaa cgccgtgtcg tacaccaccc tgatgcaggg gcttggcgcc agggggaggg | 1380 |
| ttgatgaggc aatgcgggtg tttgtggaaa tgcgcaggaa ggggtgtgca ccggattccg | 1440 |
| tcacctatgg cactctggtt actgcgttct gcaaggctgg taggatatca cagggatatg | 1500 |
| agttcttgga cgtcatggca agggagggtc tgcgggtgga cgccggcgtg tacctcgggt | 1560 |
| tcttcgtcgc gcacgagaag aaggagcagc ttgaggagtg cttggagttg atggagagga | 1620 |
| tgagggagtg caggtgcccg ccagacctca gcatctacaa tgtggtgatc aggttggcct | 1680 |
| gcaaactcgg ggagacgaag caggctgtgg cattgtggaa cgagatggag accaacgagc | 1740 |
| ttagtcccgg ggttgacaca tttgctatca tggtgactgg cctcgttggc caaggcgtgc | 1800 |
| tggttgaggc ctgcgttat ttcaaggaca tggttgggag gggactcttt gttgcacccc | 1860 |
| agtatggggt gctgaaggac ctcctcaatt cattggtcag agatcagaaa cttgagcttg | 1920 |
| caaaggatgt ttgggatgc attatgacca aaggctgtga gctcaatttt ggcgcatgga | 1980 |
| caatctggat tcatgcactg tacgcaaaga acacgtcaa ggaggcctgc atgtattgct | 2040 |
| tggacatgct tgacgctggt ctgatgccgc agcccgacac atttgcaaag ctgatgaagg | 2100 |
| gactgaagaa gctctacaac aggcagattg ctgctgagat cactgagaag gtgaggaaga | 2160 |
| tggcggagga gagacatgtt agcttcaaga tgtataagag gcgtggggtg agggatcttg | 2220 |
| aagagaagcc taaggcaaag agaaagaaag ggcagaaaag gagtcgcttg aggcaggctg | 2280 |
| gtcagaatca atccaatagg catgctgaca aaactgacct tttgatgat tttgatgatg | 2340 |
| aataatttca tgcaaggact agttttgcc ttctgatagt tgctctatat agtttcgact | 2400 |

```
tattactcta gatcattctg tgtgaggttt aatattttt ttcttgggga atcactggat    2460
ctagattgta aagttgctaa tccaaacaag tcaataaaca tgtcacaaaa aaatatattg    2520

<210> SEQ ID NO 7
<211> LENGTH: 574
<212> TYPE: DNA
<213> ORGANISM: Zea mays

<400> SEQUENCE: 7
tgatggagag gatgcgggag tgccggtgtc caccagatct caagatatac aatgtggtga      60
ttcggttggc ctgcaggctt ggggagacca agcaagccat gacattgtgg aatgagatgg     120
aaagtgctgg gctcagtcct gtggtcgata catttgctat cgtggtgagt ggccttgttg     180
ttcagggttt gctgattgag gcatgtagtt attttaaaga catggtttgg aggggctct      240 ttgtgatacc gcaatatggg gtgctgaagg acctcctcaa tgctttggtc agagatgaga     300
aacttgagct tgcaaaggat gtttggaaat gtattgtgag caaaggctgt gagctcaatg     360
tgagtgcatg gactatctgg attcatgcac tgttcgcgaa gaaacatgtc aaggaggcct     420
gcctgtattg cttagacatg ctagaggcag gactgatgcc acagcctgac acatttgcaa     480
agttgatgaa ggggctgaag aagttgtaca accgtcagat tgctgctgag attactgaga     540
aggttaggaa gatggcggag gagagacatg ttag                                574

<210> SEQ ID NO 8
<211> LENGTH: 403
<212> TYPE: DNA
<213> ORGANISM: Zea mays

<400> SEQUENCE: 8
acgcgttcga gctggcgggg cagatggagc agcgtggctg tccaccgaac gcggtgtcgt      60
acaccaccct gattcagggg cttggcgcga ggggagagt tgatgaggcc atgcgcatgt     120
ttgtggaaat gcgaaggaag gggtgcgcgc ccgatgctgt cacgtacggc accctggtta     180
acacgttttg caaggctggc aagatatccc aggggtacga gttcttggat gctatgtcga     240
gggatggcct gcggtggac gctgccgtgt accatggttt ctttgtagca cacgagaaga     300
aggagcagct tgaggagtgc ttggagctga tggagaggat gcgggagtgc cggtgtccac     360
cagatctcaa gatatacaat gtggtgattc ggttggcctg cag                       403

<210> SEQ ID NO 9
<211> LENGTH: 20
<212> TYPE: DNA
<213> ORGANISM: artificial
<220> FEATURE:
<223> OTHER INFORMATION: Synthetic primer

<400> SEQUENCE: 9
tgatggagag gatgcgggag                                                  20

<210> SEQ ID NO 10
<211> LENGTH: 21
<212> TYPE: DNA
<213> ORGANISM: Artificial
<220> FEATURE:
<223> OTHER INFORMATION: Synthetic primer

<400> SEQUENCE: 10
tgcctcaatc agcaaaccct g                                                21

<210> SEQ ID NO 11
```

```
<211> LENGTH: 27
<212> TYPE: DNA
<213> ORGANISM: Artificial
<220> FEATURE:
<223> OTHER INFORMATION: Synthetic primer

<400> SEQUENCE: 11
tggagaggat gcgggagtgc cggtgtc                                           27

<210> SEQ ID NO 12
<211> LENGTH: 27
<212> TYPE: DNA
<213> ORGANISM: Artificial
<220> FEATURE:
<223> OTHER INFORMATION: Synthetic primer

<400> SEQUENCE: 12
tggtgattcg gttggcctgc aggcttg                                           27

<210> SEQ ID NO 13
<211> LENGTH: 27
<212> TYPE: DNA
<213> ORGANISM: Artificial
<220> FEATURE:
<223> OTHER INFORMATION: Synthetic primer

<400> SEQUENCE: 13
caagcctgca ggccaaccga atcacca                                           27

<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
gcacttcttc cactggtgct                                                   20

<210> SEQ ID NO 15
<211> LENGTH: 23
<212> TYPE: DNA
<213> ORGANISM: Artificial
<220> FEATURE:
<223> OTHER INFORMATION: Synthetic primer

<400> SEQUENCE: 15
gggagcacca gtggaagaag tgc                                               23

<210> SEQ ID NO 16
<211> LENGTH: 25
<212> TYPE: DNA
<213> ORGANISM: Artificial
<220> FEATURE:
<223> OTHER INFORMATION: Synthetic primer

<400> SEQUENCE: 16
atggcgccca aggcggagaa gaagc                                             25

<210> SEQ ID NO 17
<211> LENGTH: 21
<212> TYPE: DNA
<213> ORGANISM: Artificial
<220> FEATURE:
<223> OTHER INFORMATION: Synthetic primer

<400> SEQUENCE: 17
```

-continued cgaggtgaac ttggtgacgg c        21

<210> SEQ ID NO 18
<211> LENGTH: 20
<212> TYPE: DNA
<213> ORGANISM: Artificial
<220> FEATURE:
<223> OTHER INFORMATION: Synthetic primer

<400> SEQUENCE: 18
gagggctgta cattctggga        20

<210> SEQ ID NO 19
<211> LENGTH: 20
<212> TYPE: DNA
<213> ORGANISM: Artificial
<220> FEATURE:
<223> OTHER INFORMATION: Synthetic primer

<400> SEQUENCE: 19
tcctgatcag tcacgctgtc        20

<210> SEQ ID NO 20
<211> LENGTH: 25
<212> TYPE: DNA
<213> ORGANISM: Artificial
<220> FEATURE:
<223> OTHER INFORMATION: Synthetic primer

<400> SEQUENCE: 20
cttcgtccat aatggcaatt atctc        25

<210> SEQ ID NO 21
<211> LENGTH: 20
<212> TYPE: DNA
<213> ORGANISM: Artificial
<220> FEATURE:
<223> OTHER INFORMATION: Synthetic primer

<400> SEQUENCE: 21
agctgctcct tcttctcgtg        20

<210> SEQ ID NO 22
<211> LENGTH: 20
<212> TYPE: DNA
<213> ORGANISM: Artificial
<220> FEATURE:
<223> OTHER INFORMATION: Synthetic primer

<400> SEQUENCE: 22
gcacttcttc cactggtgct        20

<210> SEQ ID NO 23
<211> LENGTH: 35
<212> TYPE: DNA
<213> ORGANISM: Artificial
<220> FEATURE:
<223> OTHER INFORMATION: Synthetic primer

<400> SEQUENCE: 23
atggatccga catgtgcatc tcagtccgcc acggg        35

<210> SEQ ID NO 24
<211> LENGTH: 26
<212> TYPE: DNA
<213> ORGANISM: Artificial
<220> FEATURE:

-continued

<223> OTHER INFORMATION: Synthetic primer

<400> SEQUENCE: 24
caatgaattc tatttcaatt agccgg         26

<210> SEQ ID NO 25
<211> LENGTH: 37
<212> TYPE: DNA
<213> ORGANISM: Artificial
<220> FEATURE:
<223> OTHER INFORMATION: Synthetic primer

<400> SEQUENCE: 25
gggtacctcg agatgcatgt attaattcat tgacacc         37

<210> SEQ ID NO 26
<211> LENGTH: 35
<212> TYPE: DNA
<213> ORGANISM: Artificial
<220> FEATURE:
<223> OTHER INFORMATION: Synthetic primer

<400> SEQUENCE: 26
ggaagcttgc gagggttaa gtactacaca agttg         35

<210> SEQ ID NO 27
<211> LENGTH: 1009
<212> TYPE: DNA
<213> ORGANISM: artificial
<220> FEATURE:
<223> OTHER INFORMATION: Synthetic probe

<400> SEQUENCE: 27
tctagacccg acgactggga cctgggccag cgactcatgc taggcggctg cgacccgctg         60
cccggccgcc gctgcctggc cccggcctcc aagctcttcc gccgcccgct gcccgtcaac        120
gagtcgctct ggacgctgtc cgacgacggc aacgtccggt ggagccgcta ccactgccgt        180
ggctacaggt gcctgtccgc caggaaccag cgccgcgcta cgaccgctgc gtggggtgct        240
tcgacatgga ccgcgagagg cagcggtggg ccaaccgcac cgcgtcgtcg tccctcgccg        300
acttcctcgt cgacgacgtg ctcgcggcga aaggggcga gtgcgcatcg ggctggacat        360
gagcgtgggc acgggcagct tgcggcgcg catgcgggag cgcggcgtga ccatcgtgtc        420
ggcggccatg aacctggggc gcgccgttcg cggagacaga tcggctgcgc ggctggtgcc        480
cctgtacacg accatgagcc agcggctgcc gctgttcgac aacaccatgg acctggtgca        540
cacggcgagg ctcttcgagg ggtgggtgga cctgcacctg ctggacttcg tgctcttcga        600
ctgggaccgc gtgctcgccc ggtgggctgc tgtgggtgga caagttgcct gcgcgcgcaa        660
ggacctggac gactacatgt acatgttcct gcagttcagg tacaagaagc accgctgggc        720
cgtctccttc aagtccaagg acgaggtcta cctgcaatgg agatttggat gtgtgttctc        780
ccaaatccaa ttttgtcctc ttcagtgaat gttcctgaat cagtagccat ttatatatat        840
catgaagtgg attgggaagg agccgaacga agttgaactg ttgaatgtca gtgaatctga        900
tgatagagca gaagttgaac agctggagga caacaaaaga gcagagtttg agtgcaattc        960
cgggggcaaa tcgcaatatc ctggactggg atactcgtga tccaagctt              1009

<210> SEQ ID NO 28
<211> LENGTH: 58
<212> TYPE: PRT
<213> ORGANISM: Unknown
<220> FEATURE:

<223> OTHER INFORMATION: Consensus sequence

<400> SEQUENCE: 28

Ala Gly Leu Met Pro Gln Pro Asp Thr Phe Ala Lys Leu Met Lys Gly
 1               5                  10                  15

Leu Lys Lys Leu Tyr Asn Arg Gln Ile Ala Ala Glu Ile Thr Glu Lys
            20                  25                  30

Val Arg Lys Met Ala Glu Glu Arg His Val Ser Phe Lys Met Tyr Lys
        35                  40                  45

Arg Arg Gly Val Arg Asp Leu Glu Glu Lys
    50                  55

<210> SEQ ID NO 29
<211> LENGTH: 30
<212> TYPE: DNA
<213> ORGANISM: Artificial
<220> FEATURE:
<223> OTHER INFORMATION: Synthetic primer

<400> SEQUENCE: 29
ccctcgagtt actcatgatg gtcatctagg                                30

<210> SEQ ID NO 30
<211> LENGTH: 32
<212> TYPE: DNA
<213> ORGANISM: Artificial
<220> FEATURE:
<223> OTHER INFORMATION: Synthetic primer

<400> SEQUENCE: 30
gctctagagg gtataacttc aactgttgac gg                             32

<210> SEQ ID NO 31
<211> LENGTH: 20
<212> TYPE: DNA
<213> ORGANISM: Artificial
<220> FEATURE:
<223> OTHER INFORMATION: Synthetic EMP4For2 primer

<400> SEQUENCE: 31
gcatgtgcat ctcagtccgc                                           20

<210> SEQ ID NO 32
<211> LENGTH: 1911
<212> TYPE: DNA
<213> ORGANISM: Artificial
<220> FEATURE:
<223> OTHER INFORMATION: Synthetic promoter BETL9

<400> SEQUENCE: 32
ctcgagttac tcatgatggt catctaggat catagaccat ccccacagac caacatgagt      60
cttttctacg cactttgttc actcgtgtgc atcaaagaaa acttcttggt tggtcactca     120
tccaaaaatt gctctgagcc aagcatgctt atcttagagg ttttttttgag ataagcttct    180 gaaaaagaag gtgcaccttg tttgtatgag tattatacca ttcctattaa gccttggaca    240
aagatatcac aatccaccta ggccaagata tcacatttcc caacttagtc tataaaagga    300
ctagacaaga catctcctta gaagagaagc cctacctctt gtgcccataa caggcacctc    360
caacttgaga actaatttca caaagagtca cgctcttggg aactccatgt actcatatgt    420
acacactaca tctaatgcat agaaacacca agatcacatt gtactagcaa aatgtcatag    480
aagactagtt aaaaccttgt ttggtctgct caaacttaac aaatcaccta ggagacatgc    540

```
tagaagtatc tcaacagaga atgacaccat atagtagtgg caccaagtgc ctaatctgca      600
cacaaaaaaa tcgtaccata catgacatca aggcttaata atagagtgta tgttaaagcg      660
agcatgcaac ctatgagtgg tatgtaggag ttaggtttaa acaaggtaat ggctcaagca      720
ccacacatcc taccacaatg tcgtaataaa ataaaaagca ctagcaatct atttagcatg      780
cctaaatggg atactatgag gttgggtggg atgtggcacc tttgtataat ggcccagttc      840
cttagtgtag tcttgatcct ccccgttatg ttgagactcc tctagggatt ttgtaggaat      900
catcaaattt tcataagcaa tttcttgtgc acaagaacc aaatagattg aaaaagtttc       960
aaattcactc aaacacaaaa ccatggcaca tagcttatgt gacaaaatat ttgggacact     1020
agtttcatat tttttgagat catataagtt tattatcaaa ctcccaagga ttaaattatt     1080
ttttgaaaaa aaagaaaaaa gggaaaacat cataaggtga cacatggcaa cctctgaatg     1140
actagacttt taccatctct caggtgggtc tggtcaacaa tcactgttgg tcggtcctta     1200
ccttgcctag acgggtcctt agtaggccta ctggggttgag ttatgggata aattgtggcc     1260
tagaaacata ccagtccacc aaccttggga ccacttaaaa aattgcatct ttcaccatta     1320
tactatttag atgttttttaa aaaacaatca taacttttac atcgaaatca aaactagaca     1380
aatttttatac tttcacagag cagcagaaat ttatacaata tgattgaata caagatgtag     1440
gacccaatgg agagaatttt ttgtctccta tatgcttgaa tacccaacat aatatcttcg     1500
caacatacta tctatctaat agaaaaatta taatatagtt aaatacttaa gtagtatcta     1560
gtggatagaa ttcaatatct cctacatgca tgaggagtaa tatctactag acatgcaaca     1620
tatttttatc tatctaatag aatatatata ataaagttaa atattatatg catcacctac     1680
tatatataat ttgatatctt ttagatgtat aagggactaa gaataatatc tctagcacac     1740
atgcaatgca ttatctatct aaatatatta tataatagtt aaatattaat tatacgtagt     1800
ctaaacctac atataagcct acccatcccc acttaaagat ctcagtgtca cacatagacc     1860
atacatctca cttcgccaaa aaaattccgt caacagttga agttataccc t              1911
```

```
<210> SEQ ID NO 33
<211> LENGTH: 35
<212> TYPE: PRT
<213> ORGANISM: Artificial
<220> FEATURE:
<223> OTHER INFORMATION: Synthetic consensus sequence

<400> SEQUENCE: 33
```

Asp Val Val Thr Tyr Asn Thr Leu Ile Ser Gly Leu Cys Lys Ala Gly
1               5                   10                  15

Arg Leu Glu Glu Ala Leu Glu Leu Phe Glu Glu Met Lys Glu Lys Gly
            20                  25                  30

Ile Ala Pro
        35

```
<210> SEQ ID NO 34
<211> LENGTH: 51
<212> TYPE: PRT
<213> ORGANISM: Arabidopsis thaliana

<400> SEQUENCE: 34
```

Leu Tyr Asn Arg Thr Ile Ala Ala Glu Ile Thr Glu Lys Val Val Lys
1               5                   10                  15

Met Ala Ser Glu Arg Glu Met Ser Phe Lys Met Tyr Lys Lys Lys Gly
            20                  25                  30

Glu Glu Asp Leu Ile Glu Lys Ala Lys Pro Lys Gly Asn Lys Glu Gly

-continued

```
                35                  40                  45

Lys Lys Lys
    50

<210> SEQ ID NO 35
<211> LENGTH: 55
<212> TYPE: PRT
<213> ORGANISM: Arabidopsis thaliana

<400> SEQUENCE: 35

Leu Tyr Asn Arg Glu Phe Ala Gly Glu Ile Thr Glu Lys Val Arg Asn
1               5                   10                  15

Met Ala Ala Glu Arg Glu Met Ser Phe Lys Met Tyr Lys Arg Arg Gly
            20                  25                  30

Val Gln Asp Leu Thr Glu Lys Ala Lys Ser Lys Gln Asp Arg Glu Gly
        35                  40                  45

Lys Lys Lys Gln Arg Ser Arg
    50                  55
```